US006579721B1

(12) United States Patent
Natan et al.

(10) Patent No.: US 6,579,721 B1
(45) Date of Patent: Jun. 17, 2003

(54) BIOSENSING USING SURFACE PLASMON RESONANCE

(75) Inventors: Michael J. Natan, Los Altos, CA (US); David J. Pena, State College, PA (US); Glenn Goodrich, State College, PA (US); Lin He, Mountain View, CA (US); L. Andrew Lyon, Marietta, GA (US); Michael D. Musick, Huntingdon Valley, PA (US); William D. Holliway, Atlanta, GA (US)

(73) Assignee: SurroMed, Inc., Palo Alto, CA (US)

( * ) Notice: Subject to any disclaimer, the term of this patent is extended or adjusted under 35 U.S.C. 154(b) by 0 days.

(21) Appl. No.: 09/711,748

(22) Filed: Nov. 13, 2000

Related U.S. Application Data

(63) Continuation of application No. 09/629,790, filed on Jul. 31, 2000.
(60) Provisional application No. 60/165,075, filed on Nov. 12, 1999, provisional application No. 60/170,682, filed on Dec. 14, 1999, provisional application No. 60/168,831, filed on Dec. 3, 1999, provisional application No. 60/163,789, filed on Nov. 5, 1999, provisional application No. 60/146,606, filed on Jul. 30, 1999, provisional application No. 60/146,694, filed on Jul. 30, 1999, provisional application No. 60/146,694, filed on Jul. 30, 1999, provisional application No. 60/190,394, filed on Mar. 17, 2000, and provisional application No. 60/198,699, filed on Apr. 20, 2000.

(51) Int. Cl.$^7$ .............................................. G01N 21/65
(52) U.S. Cl. ........................ 436/164; 436/525; 356/445
(58) Field of Search ..................... 385/12, 129, 130, 385/131; 422/82.05, 82.11; 436/164, 165, 171, 518, 524, 525, 527, 805, 172; 356/300, 301, 445

(56) References Cited

U.S. PATENT DOCUMENTS

| | | | |
|---|---|---|---|
| 5,436,161 A | | 7/1995 | Bergstrom et al. |
| 5,606,633 A | * | 2/1997 | Groger et al. ............... 385/12 |
| 5,609,907 A | | 3/1997 | Natan et al. |
| 5,716,854 A | | 2/1998 | Lofas et al. |
| 5,776,785 A | | 7/1998 | Lin et al. |
| 5,955,729 A | | 9/1999 | Nelson et al. |
| 6,025,202 A | | 2/2000 | Natan |
| 6,066,448 A | | 5/2000 | Wohlstadter et al. |
| 6,068,752 A | | 5/2000 | Dubrow et al. |
| 6,149,868 A | | 11/2000 | Natan et al. |

FOREIGN PATENT DOCUMENTS

| EP | 0 276 142 B1 | 1/1988 |
|---|---|---|
| WO | WO 98/04740 | 2/1998 |
| WO | WO-9810289 * | 3/1998 |

OTHER PUBLICATIONS

Johne et al. (1995) Journal of Immunological Methods 167–174.
Kukanskis et al. (1999) Anal. Biochem. 274:7–17.
Lyon et al. (1998) Anal. Chem. 70:5177–5183.
Lyon et al. (1999) Rev. Sci. Instrum. 70:2076–2081.
Lyon et al. (1999) Sens. Actuators, B 54:118–124.
Lyon J. (1999) Phys. Chem. B 103:5826–5831.
Mirkin et al. (1996) Nature 382: 607–609.
Mucic et al. (1998) J. Am. Chem. Soc. 120: 12674–12675.
Nelson et al. (1999) Anal. Chem. 71, 3928–3934.
Peterlinz et al.(1997) J. Am. Chem. Soc. 119:3401.
Storhoff and Mirkin (1999) Chem. Rev. 99:1849–1862.
Storhoff et al. (1998) J. Am. Chem. Soc. 120: 1959–1964.
Averitt et al. (1997) Phys. Rev. Lett. 78:4217–4220.
Bier, et al. (1997) Sens. Actuators, B, 38–39, 78–82.
Bowtell, Nat. (1999) Genet. Suppl. 21:20–24.
Brockman et al. (1999) J. Am. Chem. Soc. 121:8044.
Choi et al. (1998) J. Microbiology 36:43–48.
Elghanian et al. (1997) Science 277: 1078–1081.
Feriotto et al. (1999) Human Mutation 13:390–400.
Frutos et al. (1998) Anal. Chem. 70, 449A–455A.
Frutos et al. (1999) Anal. Chem. 71, 3935–3940.
Grabar et al. (1995) J. Anal. Chem. 67: 735–743.
Grabar et al. (1996) J. Am. Chem. Soc. 118:1148–1153.
Gu et al. (1998) Supremol. Sci. 5:695–698.
Herne et al. (1997) J. Am. Chem. Soc. 119:8916–8920.
Kai et al. (1999) Anal. Chem. 71:796–800.
Keating et al. (1998) J. Phys. Chem. B 102, 9404–9413.
Keating et al. (1998) J. Phys. Chem. B 102, 9414–9425.
Buckle et al. (1993) Biosens. & Bioelectronics 8:355–363.
Hanken et al. (1998) in Electroanalytical Chemistry 20:141–225 (Bard and Rubinstein, eds.).
Thiel et al. (1997) Anal. Chem. 69:4948–4956.

* cited by examiner

*Primary Examiner*—Jeffrey Snay
(74) *Attorney, Agent, or Firm*—Swanson & Bratschun, LLC

(57) ABSTRACT

The invention provides methods and reagents for the enhancement of surface plasmon resonance (SPR)-based detection assays. The methods and reagents can be used in any molecular recognition assay that uses a solid support. The invention also provides an SPR instrument that operates in imaging mode.

10 Claims, 13 Drawing Sheets

▼ = ANTIGEN
◯ = Au COLLOID
Y = ANTIBODY

ANGLE, DEGREES

SEQUENCE LISTING

<160> NUMBER OF SEQ ID NOS: 3

<210> SEQ ID NO 1
<211> LENGTH: 12
<212> TYPE: DNA

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' end is modified with a C6H12-NH2 moiety

<400> SEQUENCE: 1
cgcattcagg at                                                          12

<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2
tacgagttga gaatcctgaa tgcg                                             24

<210> SEQ ID NO 3
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: 3' end is modified with a C6H12-SH moiety

<400> SEQUENCE: 3
tctcaactcg ta                                                          12
```

BIOSENSING USING SURFACE PLASMON RESONANCE

RELATED APPLICATIONS

This application claims the benefit of the filing date of U.S. Provisional Application Ser. No. 60/165,075, entitled "Biosensing Using Colloidal Au-Amplified Spectroscopies," filed Nov. 12, 1999, and U.S. Provisional Application Ser. No. 60/170,682, entitled "PDMS Microwell Arrays," filed Dec. 14, 1999. This application is also filed as a Continuation-in-Part of U.S. application Ser. No. 09/629,790, entitled "Instruments, Methods and Reagents for Surface Plasmon Resonance," filed Jul. 31, 2000. U.S. application Ser. No. 09/629,790 was filed claiming the benefit of U.S. Provisional Application Ser. No. 60/168,831, entitled "An Improved Surface Plasmon Resonance Apparatus," filed Dec. 3, 1999, U.S. Provisional Application Ser. No. 60/163,789, entitled "Colloidal Metal Amplified Surface Plasmon Resonance (SPR)," filed Nov. 5, 1999, U.S. Provisional Application Ser. No. 60/146,606, entitled "Distance-Magnified Colloidal Metal-Amplified Surface Plasmon Resonance (SPR)," filed Jul. 30, 1999, U.S. Provisional Application Ser. No. 60/146,694, entitled "Ultrasensitive Detection of DNA by Surface Plasmon Resonance (SPR)," filed Jul. 30, 1999, U.S. Provisional Application Ser. No. 60/190,394, entitled "SPR Detection of DNA Hybridization," filed Mar. 17, 2000, and U.S. Provisional Application Ser. No. 60/198,699 entitled "Colloidal Au-Enhanced Surface Plasmon Resonance for Ultrasensitive Detection of DNA Hybridization," filed Apr. 20, 2000, all of which are incorporated herein by reference in their entirety.

FIELD OF THE INVENTION

The present invention relates generally to surface plasmon resonance sensors. In particular, the present invention relates to instruments, methods and reagents for amplifying the surface plasmon resonance response and increasing its sensitivity, flexibility, throughput, specificity, and scope.

BACKGROUND OF THE INVENTION

Surface plasmon resonance (SPR) is a general spectroscopic method for sensing refractive index changes near the surface of a metal film. Its sensitivity to these changes provides a versatile platform for the observation and quantitation of chemical reactions at the metal/solution interface, provided the chemistry is well-designed. The generality of the technique has led to its application to a variety of chemical systems, including biosensing (where specifically designed commercial instrumentation is available).

SPR allows detection of small changes in refractive index that result from interactions between surface-confined biomolecules and solution-borne species. For example, immobilization of a protein to the sensor surface allows for detection of protein binding events manifested by a change in refractive index and hence a change in the angle-dependent reflectance of the metal film. This type of SPR sensing is typically carried out on commercial instruments that use a carboxylated dextran gel on a Au film as the sensor surface, where the gel acts as a host for the surface-confined binding partner. However, SPR has been applied in a number of other formats, including imaging SPR where a large number of chemistries can be rapidly interrogated simultaneously. Likewise, a variety of other surface chemistries have been used as scaffolds for measurements of biomolecular interactions.

SPR relies on the optical excitation of surface modes (plasmons) in a free electron metal (e.g., a 50 nm thick film of Au, Ag, Al, or Cu anchored to a glass substrate by a thin adhesion layer of Ti, Cr, or mercaptosilane). Back-side, p-polarized illumination of a prism-coupled film at some angle greater than the critical angle for total internal reflection results in plasmon excitation at the metal-solution interface. Plasmon excitation is observed as an increase in optical absorbance (decrease in reflectance) at an optimal coupling angle. This, in turn, results in a minimum in the SPR profile (a plot of reflectance versus angle), which is referred to as the plasmon angle ($\theta_p$). Sensing via SPR is possible due to the sensitivity of $\theta_p$ to changes in the index of refraction near the metal surface. Adsorption, desorption, and molecule-molecule interactions that occur at the metal-solution interface result in such changes, thereby inducing a shift in plasmon angle. These changes can be monitored in real-time, making SPR suitable for dynamic sensing.

Perhaps the most widely studied subset of chemistries using SPR is protein-protein interactions, where binding event signal transduction is difficult or impossible to accomplish by traditional optical spectroscopies. In order to decrease nonspecific binding and to increase surface loading of biomolecules, SPR experiments conducted on commercial instrumentation commonly use an extended coupling matrix in conjunction with the sensing surface. Such measurements typically begin with one protein immobilized on proprietary substrates comprising a carboxylated dextran (or "extended coupling") matrix layered on top of a thin evaporated Au film (i.e., between the film and the sample). The result is an extended three-dimensional array of molecules extending some 200 nm away from the surface of the Au film. Protein binding events leading to small changes in the refractive index of the dextran layer are detected via correspondingly small changes in the angle-dependent attenuated total reflectance. Despite the signal amplification afforded by the dextran matrix, the detection of small (<1000 MW) molecules is still a non-trivial task for commercial instrumentation. In some cases even the detection of species in the 2,000–10,000 MW range can prove challenging.

Use of coupling matrices is associated with a number of additional drawbacks, including the possibility of nonspecific interactions with biomolecules that dominate the signal, and the exclusion of large proteins. Furthermore, improper orientation of biomolecules within the matrix often leads to low biomolecular activity, especially with proteins. Because mass transport to molecules immobilized in the matrix is commonly pH dependent, separate steps are required to optimize diffusion of reagents into the matrix during the assay. These shortcomings can create significant difficulties in assay design. It would be desirable to avoid these problems by using planar SPR substrates (i.e., without an overlying matrix) such as Au films modified with a monolayer of a bifunctional organic crosslinker. However, SPR reflectivity changes within these more uniform substrates are often too small to be measurable in any practical assay.

The applicability and usefulness of SPR could be greatly expanded if ligand binding events resulted in more pronounced changes in refractive index and, hence, more pronounced shifts in plasmon angle. Such increased sensitivity could make the technique broadly applicable to high-throughput screening of low molecular-weight drug candidates.

It is an object of the present invention to provide instruments, methods and reagents for the amplification of SPR reflectivity changes in chemical assays, especially in biomolecular recognition assays on planar SPR substrates coated with a monolayer or submonolayer of capture reagents (e.g., antibodies). It is also an object of the invention to provide methods and reagents for ultra-sensitive, non-PCR-based DNA detection assays. It is moreover an object of this invention to describe an SPR-based method for measuring distances between surface-confined objects on the scale from 1 to 500 nm, with 3-Angstrom resolution.

An additional object of this invention is to enable high throughput screening reactions (both primary and secondary) by amplified imaging SPR.

A further object of the invention is to provide a "wet chemistry" method for the synthesis of Au films for SPR (or other surface spectroscopies) as a replacement for (or alternative to) cumbersome evaporative methods used in the art.

Finally, it is an object of the invention to provide an imaging SPR instrument capable of depicting spatial differences in film reflectance at fixed angles of incidence, which spatial differences are induced by differential indices of refraction or film thickness (i.e., differential chemical modification). The imaging SPR instrument provided by the invention allows SPR to be used in multiplexed biological "chip" assay formats. For example, the imaging SPR instrument would be integral in the simultaneous detection of multiple target analytes using a solid support to which ligands for the different target analytes are attached at specific locations.

The instrumentation, methods, and reagents of the present invention enable chemical assays (including multiplexed biosensing assays) of unprecedented sensitivity and selectivity.

SUMMARY OF THE INVENTION

The present invention provides instrumentation, methods, and reagents for the amplification of SPR reflectivity changes. In one series of embodiments, colloidal-metal nanoparticles are used as optical tags for SPR-based sensing assays. These embodiments rely on the observation that the SPR response of a metal film changes dramatically upon localization of such colloidal-metal nanoparticles to the film surface. The dramatic change in the SPR response of metal films that occurs upon adsorption of colloidal metal nanoparticles can be exploited in any assay that depends on the occurrence of a molecular recognition event (e.g., the binding of antigen to an antibody, the binding of a ligand to its receptor, or the hybridization of complementary nucleic acid molecules). In one of the many possible implementations, one of the molecules that participates in a molecular recognition event is immobilized on the surface of a metal film of the SPR substrate (or to an entity attached to the metal film). Another molecule that participates in the interaction with the immobilized molecule—either by binding directly to the immobilized molecule, or by binding to a third molecule that in turn binds to the immobilized molecule—is then tagged with the colloidal metal nanoparticle. The binding between the participating molecules leads to colloidal metal adsorption, with the concomitant change in the SPR response of the film. Methods are well known in the art for preparing monodisperse colloidal metal nanoparticles in solution, as are methods for attaching biomolecules to the metal nanoparticles without loss of biological activity. In some embodiments, the use of colloidal Au nanoparticles leads to a 100,000-fold increase in SPR sensitivity.

For example, colloidal Au nanoparticles can be readily attached to ligands of target analytes. Then, when the target analyte becomes localized to the surface of the SPR film (or to ligands immobilized thereon), the Au-tagged ligands are brought to the surface when the ligands bind the target analyte, leading to the amplified changes in SPR reflectivity. The amplification in signal is sufficiently large that planar SPR substrates (such as a Au film modified with a bifunctional organic cross linker) can be used, thus avoiding several of the problems associated with commercial dextran-based matrices.

Notwithstanding the significant limitations discussed above, dextran-based SPR substrates are adequate for some types of assay. For this reason, the invention also provides methods for the amplification of SPR reflectivity within dextran-based matrices. In some embodiments of the invention, Au nanoparticles attached to ligands are first brought to the matrix and retained there through the biomolecular interaction that forms the basis of the assay. The nanoparticles are chosen to be of a sufficiently small diameter to permit efficient diffusion into the network. However, nanoparticles of this size do not optimally amplify changes in SPR reflectivity. Consequently, to optimize amplification, the nanoparticles are then enlarged through addition of an Ag plating solution.

In other embodiments, the invention provides a method for further enhancing colloidal Au-amplified SPR reflectivity by overlaying an inorganic film over the Au surface. The distance between the metallic nanoparticles and the metal surface has a significant impact on SPR reflectivity. In preferred embodiments, a 30 nm thick film of $SiO_2$ is evaporated onto a 50 nm Au surface. When colloidal gold nanoparticles become attached to this surface—either directly or by way of, e.g., a protein-protein interaction—the $SiO_2$ layer acts as a spacer to optimize the coupling distance between the Au nanoparticles and the Au surface. This leads to a greater shift in the plasmon angle (i.e., angle of minimum reflectance) than observed using colloidal Au nanoparticles and a Au surface without an $SiO_2$ film. The enhancement is observed even when the Au surface is bound to very low levels of colloidal Au (e.g., less than 1% surface coverage).

In another series of embodiments, the methods are used to provide a "sandwich" immunoassay. Specifically, a primary "capture" antibody to a target analyte is immobilized on the surface of an SPR substrate, either on the Au surface itself, or on an overlaying $SiO_2$ film (or other material). A secondary antibody to the target analyte is conjugated to colloidal Au nanoparticles by one of a variety of methods. The Au nanoparticles and the SPR substrate are then contacted with a biological fluid suspected of containing the target analyte. If present, the target analyte will become bound to the SPR substrate through its interaction with the immobilized capture antibody, and the colloidal Au will become localized to the SPR substrate through the interaction between the secondary antibody and the bound target analyte. As a result, an amplified change in the plasmon angle will be observed, amplified with respect to the angle shift observed if the secondary antibody was not conjugated to colloidal Au nanoparticle. In some cases, the methods provided herein provide a 100,000-fold or greater enhancement in SPR signal relative to conventional SPR assays using dextran-based capture matrices, and provide the capability for detecting protein concentrations of less than 70 fM. It should be clear to those skilled in the art that such assays can be carried out in separate steps, in which the analyte-containing solution is first exposed to the surface, and wash steps are carried out to eliminate non-specific binding. Then, in a second step, the colloidal Au:antibody conjugate is introduced.

In another series of embodiments, the methods of the invention are applied to detect target nucleic acid sequences.

For example, a "first nucleic acid probe" may be immobilized on the surface of a planar SPR substrate and a "second nucleic acid probe" conjugated to colloidal Au nanoparticles. The probes have regions at least partially complementary to the target nucleic acid sequence (or are capable of some other interaction) such that in the presence of the target sequence, both the probes become associated therewith. As a result, the colloidal Au nanoparticles conjugated to the second nucleic acid probe become localized to the SPR substrate and there is an amplified plasmon angle shift. The methods of the invention enable a quantitation limit of better than $8 \times 10^7$ molecules/cm$^2$ for a 24-mer oligonucleotide with approximately 5 decades of dynamic range. This is more than a 1000-fold improvement in the sensitivity observed without using the amplifying methods of the invention. In this embodiment as well, introduction of the second nucleic acid probe can occur before, at the same time, or after introduction of the target sequence.

The invention also provides an SPR instrument capable of operating in imaging mode rather than scanning mode. Scanning mode SPR measures a single SPR reflectivity value for the entire SPR substrate at each angle of incidence (and/or wavelength of the incident light) within a specified range. The imaging mode instrument uses a charge-coupled device (CCD) to provide an image that depicts local SPR reflectivity values throughout an SPR substrate at one or more predetermined angles of incidence. The angle(s) of incidence chosen is the angle at which the largest change in SPR reflectivity is observed upon occurrence of the event to be assayed (e.g., upon the binding of an immobilized ligand to its target). This enables SPR to be used as the basis for detection in microarray format for the purpose of multiplexed assays. In such assays, the SPR instrument captures a normalized reflectance image of the SPR substrate after addition of the fluid suspected of containing the target analyte. In the resulting image, the intensity of the reflectance signal in each "spot" on the substrate yields information about the amount of target analyte present at that location. The imaging SPR apparatus described herein allows for the simple introduction of large samples (up to 50 mm×50 mm microarray substrates, using commercially available optics). Moreover, with custom optics, much larger surfaces, e.g., 6 inches×6 inches, can be used. Unlike previously described SPR instruments, the imaging device of the present invention provides a unique horizontal sample geometry that enables the robotic manipulators to control substrate handling and liquid delivery. This geometry obviates the need to flow solutions onto a vertical SPR substrate, as is required in prior art instrumentation.

Modifications to particles and/or surfaces aimed at increasing sensitivity and selectivity of SPR include the use of: (i) new types of metal nanoparticles such as AuS/Au core-shell particles, designed to optimize the wavelength-dependent component of dipolar coupling to surfaces; (ii) particles with sophisticated surface functionalization that exhibit reduced non-specific binding and that allow control over the number of biomolecules bound to the particle; (iii) substrates with sub-wavelength holes designed to provide local field enhancement; and (iv) oxide-coated metal films that optimize the distance dependent component of particle-surface coupling. Instrumental approaches to increased sensitivity include the use of tuned excitation wavelengths, measurement of angle-dependent surface plasmon scattering in parallel with SPR, and interferometric SPR. A third line of embodiments to improve SPR sensitivity involves the use of two secondary signal amplification schemes. One is based on particle "development", in which selective chemistries are used to grow the dimensions of immobilized particles; a second is based on a cascade effect in which molecular recognition-induced binding of one metal nanoparticle leads to selective deposition of several others from solution.

To define regions of the SPR substrate for different chemistries, a method has been developed for producing disposable replicas of printed circuit boards. The resulting "nanobeakers" (fabricated from polydimethylsiloxane, or PDMS) allow the ability to individually address a large number of spatially distinct regions over a small surface. Use of such microwell assays have illustrated that changes in Au particle coverage of less than 0.1% of a monolayer are easily detected by imaging SPR.

DETAILED DESCRIPTION OF THE PREFERRED EMBODIMENTS

Figure 1:
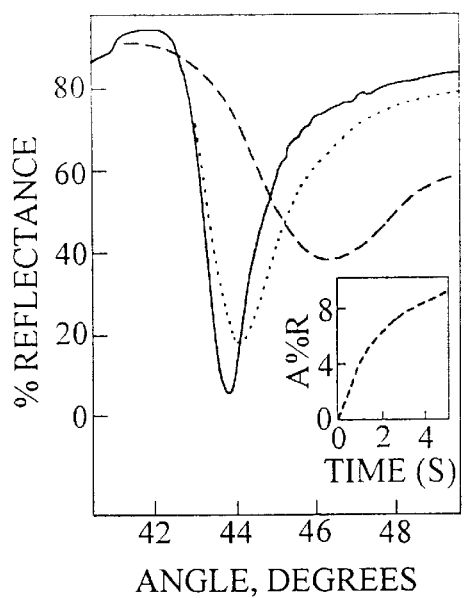
FIG. 1 illustrates the changes in the SPR profile of a 50 nm thick Au film SPR substrate that result from adsorption of 11 nm diameter colloidal Au nanoparticles.

The present invention provides a number of detailed protocols for ultra-sensitive biosensing assays that are enabled by this generalized sensing scheme. However, to aid in the understanding of the invention, a detailed description is also provided of the enhancement of the SPR response observed with adsorption (via a molecular interaction) of colloidal metal onto the metal film of the SPR substrate. The following definitions are also provided:

By "SPR substrate" is meant any material in which the phenomenon of surface plasmon resonance can be observed (i.e., the optical excitation of surface modes (plasmons) in a free electron metal when coupled to a prism). In preferred embodiments, SPR substrates comprise free electron metal films deposited or seeded onto a glass surface. Free electron metals include, but are not limited to, Au, Ag, Al, and Cu. The invention also contemplates the use of alloys or mixtures of metals.

By "SPR reflectivity" (or "reflectance") is meant the modulation of the intensity of light reflected from a prism to which an SPR substrate has been coupled. SPR reflectivity is at a minimum when surface plasmons are excited in the SPR substrate. Depending on the angle of incidence, SPR reflectivity values can range from 0% to 100% of the original intensity of the incident illumination.

By "SPR profile" is meant the value of SPR reflectivity of an SPR substrate at various angles of incidence (or at various wavelengths of incident light). SPR profiles are often depicted graphically as a plot of SPR reflectivity versus angle of incidence (or versus wavelength of incident light). By "angle of incidence" is meant the angle at which light entering a prism encounters the face of the prism to which the SPR substrate is coupled.

By "prism" is meant any optical element coupled with the SPR substrate through which incident light is directed, e.g., a polished SF11 glass onto which a film of Au has been evaporated. The preferred prisms of the instant invention include triangular prisms, most preferably with a 70°-70°-40° geometry, and hemispherical prisms.

Many of the examples and embodiments herein describe the use of Au film and colloidal Au nanoparticles, but it is to be understood that any other metal (including alloys and mixtures of metals) with an SPR response is also contemplated by and within the scope of the invention. Likewise, although examples of the methods of the present invention described herein are often directed to biosensing assays, the methods are also applicable to other SPR-based sensing configurations.

An important aspect of the present invention is the ability to multiplex assays using the SPR techniques of the present invention. Spatial multiplexing (i.e. arraying) is made possible by the physical separation of reagents on the metal substrate. However, additional multiplexing can be achieved by altering characteristics of the metal nanoparticles. Variables include changing the size and composition of the metal colloidal nanoparticles. Such multiplexing is best interrogated using traditional SPR, where the reflectivity of a film (as well as scattering therefrom) can be rapidly measured at every angle of incidence. However, multiplexing can be carried out using imaging SPR, potentially in conjunction with both light reflectance and scattering, and ideally after the reflectivity is measured as a function of incident angle.

FIG. 1 illustrates the changes in the SPR response that accompany colloidal Au adsorption to a Au film. To generate the SPR profile (reflectance as a function of incidence angle), a 50 nm thick Au film was modified with the bifunctional organic linker 2-mercaptoethylamine (MEA). The thiol group of MEA binds to the Au film, leaving free amine groups exposed on the surface. The solid line trace shows a sharp plasmon minimum (minimum reflectance value) at an angle of 43.7°. When the Au film is exposed to a 17 nM solution of 11 nm-diameter colloidal Au for 1 minute, Au particles bind to the Au film via these free amine groups. As shown by the dotted line trace in FIG. 1, this results in a significant increase in the minimum reflectance value, a broadening of the SPR profile, and a 0.2° shift in the plasmon angle.

Exposing the Au film to the colloidal Au nanoparticles for an increased period of time was found to increase the magnitude of these changes. Thus, a 60 minute exposure resulted in a plasmon angle shift of 2.6° (i.e., to 46.3°) with an increase in the minimum reflectance value by nearly 40% over that of the Au film without any localized colloidal Au nanoparticles (a "bare" Au film). This is illustrated by the dashed line trace in FIG. 1. A more complete discussion of the materials and methods used to generate the SPR profile in FIG. 1 are provided in Example 1.

These results resemble the dramatic shifts induced by thin carbon coatings evaporated onto Ag surfaces, where the strong absorptivity of the film induces a significant degree of plasmon damping. Without wishing to be bound by a single theory or mechanism, it seems likely that a similar absorptive damping process is responsible for the SPR changes due to Au-colloid adsorption, as these particles possess a non-zero imaginary dielectric component. A second possible, and non-exclusive, mechanism for damping involves the coupling of the localized surface plasmon of the colloid with the propagating plasmon in the Au film, a situation that is similar to effects observed at roughened Au films and other particle-modified films.

When the time course of the change in reflectance is monitored at the reflectance minimum, a >1% reflectance change is easily observed in the first 100 ms of colloid adsorption. The surface coverage at this time is roughly 0.1% of a close-packed monolayer. If it is assumed that the plasmon angle changes linearly with surface coverage (a reasonable assumption for low coverages), and an instrumental angular resolution limit of 0.005°, a 40-fold (0.2°/0.005°) decrease in surface coverage is detectable. Accordingly, 0.0025% of a monolayer of 12 nm-diameter colloidal Au ($2.0 \times 10^7$ particles/cm$^2$) is easily observable. As discussed below, even lower coverages are observable using larger diameter Au colloid. The time course of change in reflectance as a function of time is shown in the inset to FIG. 1.

Figure 2:
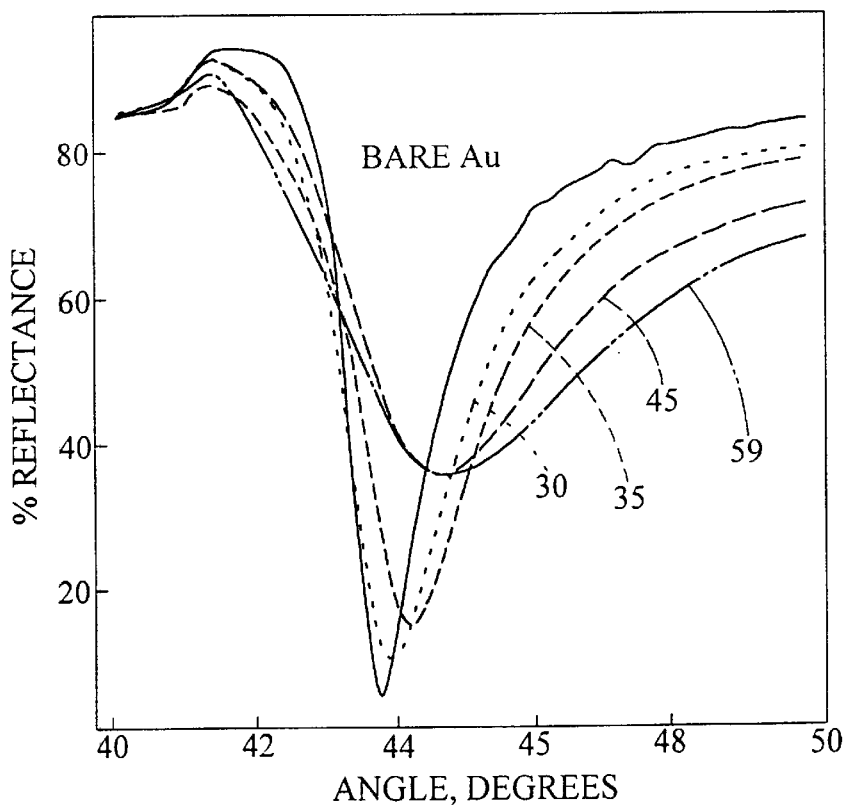
FIG. 2 illustrates how the SPR profile of a 47 nm thick Au film changes upon adsorption of colloidal Au nanoparticles of size 30 nm–59 mn.

The effect that colloidal Au adsorption has on the SPR response of a Au film substrate depends dramatically on the size of the colloidal nanoparticles. The solid line trace of FIG. 2 shows the SPR response of 47 nm thick Au films coated with MEA and then subsequently coated with similar number densities ($1.3\pm0.15\times10^9$ particles/cm$^2$) of 30, 35, 45, and 59 nm diameter colloidal Au. Despite the relatively low number density, the SPR profile changes dramatically with particle size, as the minimum reflectance increases from 10% to 35% over a less than 2-fold increase in diameter. Indeed, for the largest particle site (59 nm), the SPR profile bears little resemblance to that of a bare evaporated film; the profile is very shallow and broad, without the well-defined plasmon minimum that is typically observed in SPR. A more complete discussion of the materials and methods used to generate the SPR profile in FIG. 2 are provided in Example 1.

It is important to note that, while the number of colloidal Au particles per unit area is being held constant for the data shown in FIG. 2, the fractional surface coverage is varying with particle size. In other words, an equal number of two different size particles will cover different geometric areas. Taking this into account, the fractional coverage of 30, 35, 45, and 59 nm diameter Au particles are 1.2, 1.6, 2.6, and 4.5% of a close packed monolayer, respectively.

Figure 3A:
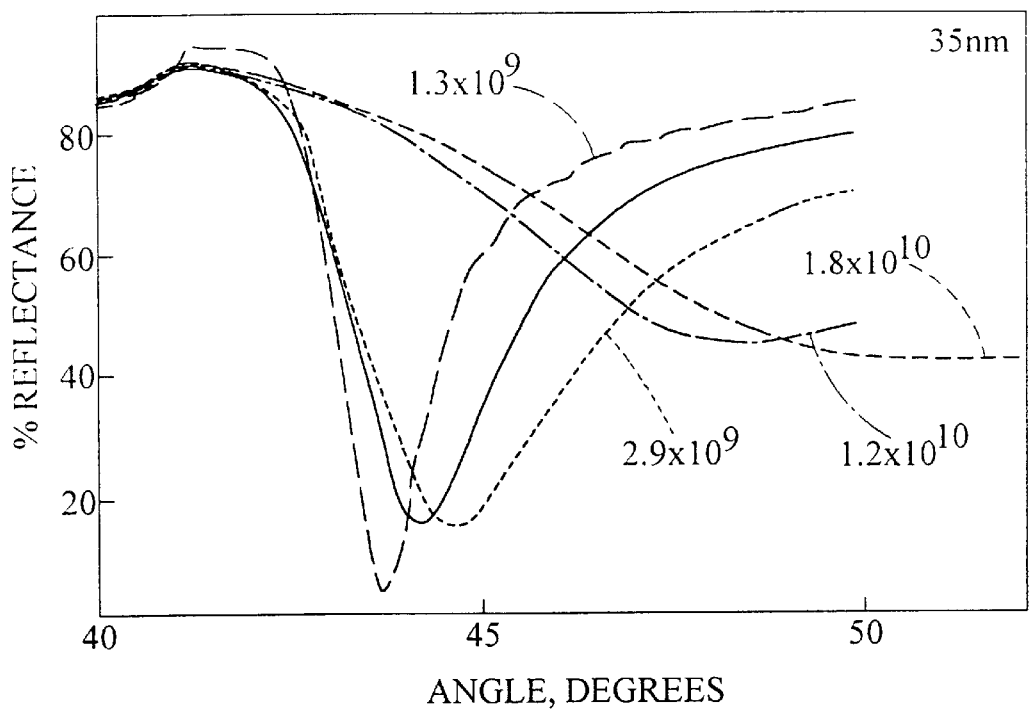
FIGS. 3A and 3B illustrate how the SPR profile of a Au film changes with different surface coverages of 35 nm (FIG. 3A) and 45 nm (FIG. 3B) colloidal Au nanoparticles.
Figure 3B:
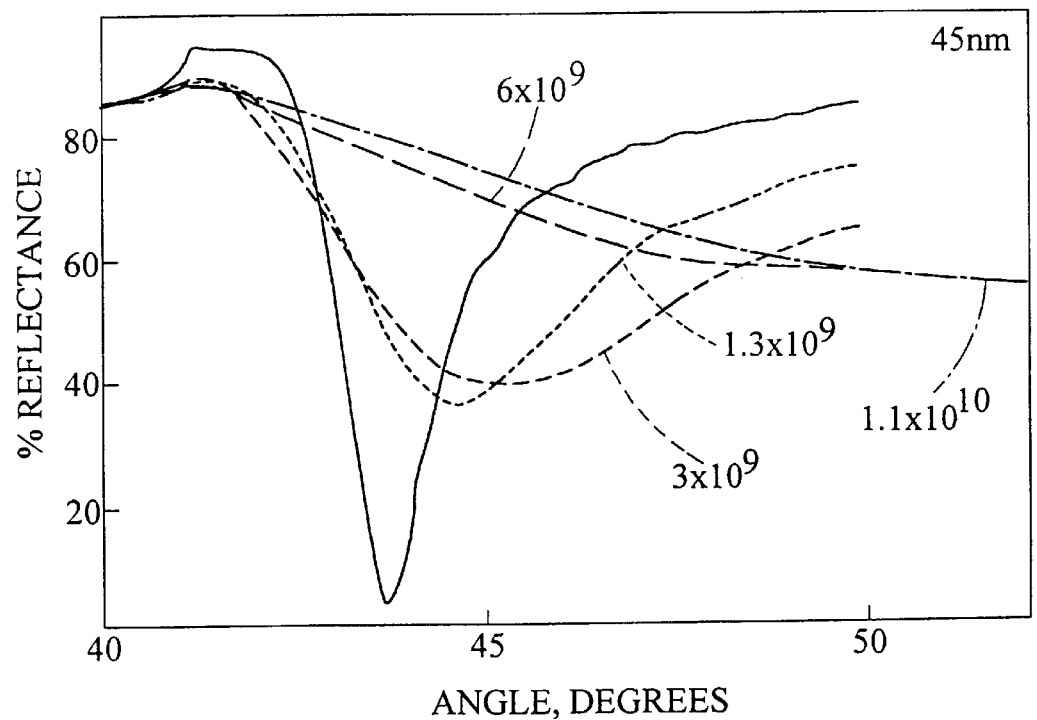

FIG. 3 shows the changes that occur in the SPR profile as a function of surface concentration (expressed as the number of particles/cm$^2$) for 35 nm (FIG. 3A) and 45 nm (FIG. 3B) diameter colloidal Au particles. In the case of 35 nm particles, a low number density of particles induces relatively small plasmon angle shifts and reflectance changes. As the number density is increased, changes in the position and the magnitude of minimum reflectance become larger, eventually attaining a total plasmon shift of about 7° and a reflectance increase of >40%. Somewhat larger angle shifts are observed with respect to the 45 nm diameter colloid Au particles; the initial change in plasmon angle is significant and increases rapidly with increasing surface concentration. However, the shape of the SPR profile evolves much more rapidly in the case of the 45 nm particle, as a >30% reflectance is observed at the lowest surface concentration. The trend is similar for other sizes of colloidal Au particle— smaller perturbations are observed for 30 nm diameter particles and much larger initial reflectance changes are observed for 59 nm diameter particles.

From a practical standpoint, it is not the gross perturbation of the profile that is important in an SPR sensing format but rather the maximum change (either an increase or decrease) that can be observed in either the plasmon angle shift or in the reflectance. It is evident from the data shown in FIGS. 2 and 3 that, at higher surface coverage, the SPR profile becomes rather too broad for accurate plasmon angle determination. Therefore, in preferred embodiments, it is more practical from both an instrumental and a sensitivity standpoint to measure the reflectance change at a single angle, despite the fact that the reflectance change itself may possess no clear physical meaning in terms of the interfacial dielectric properties.

Figure 4A:
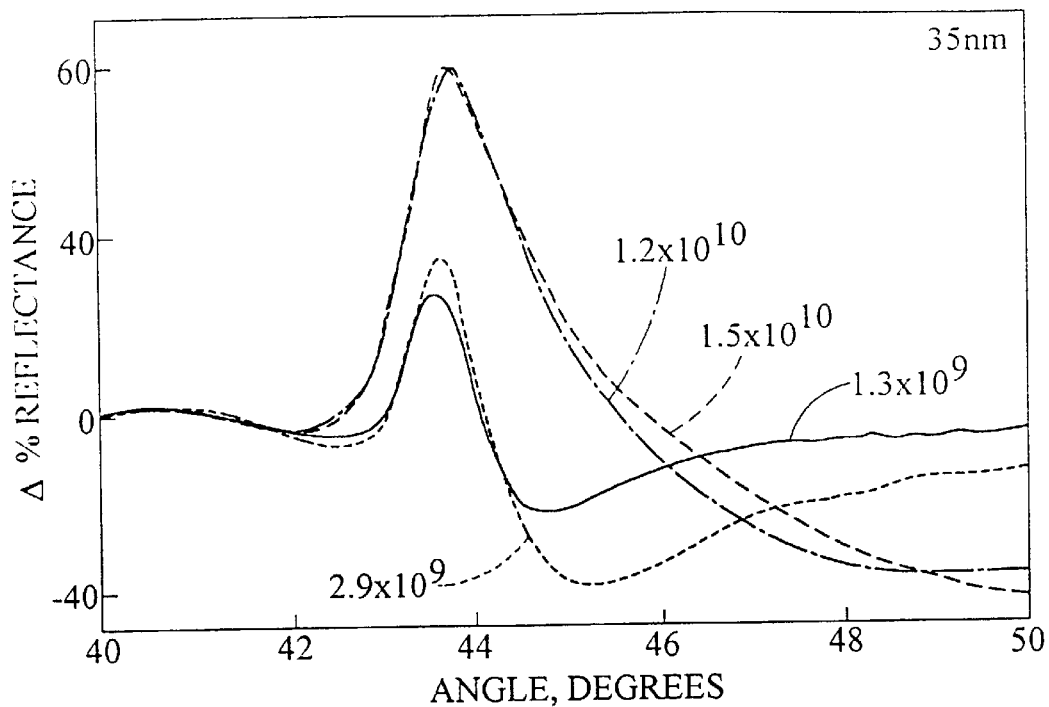
FIGS. 4A and 4B illustrate differential SPR profiles (angle of incidence versus percentage change ($\Delta$) in reflectance) for the data presented in FIG. 3.
Figure 4B:
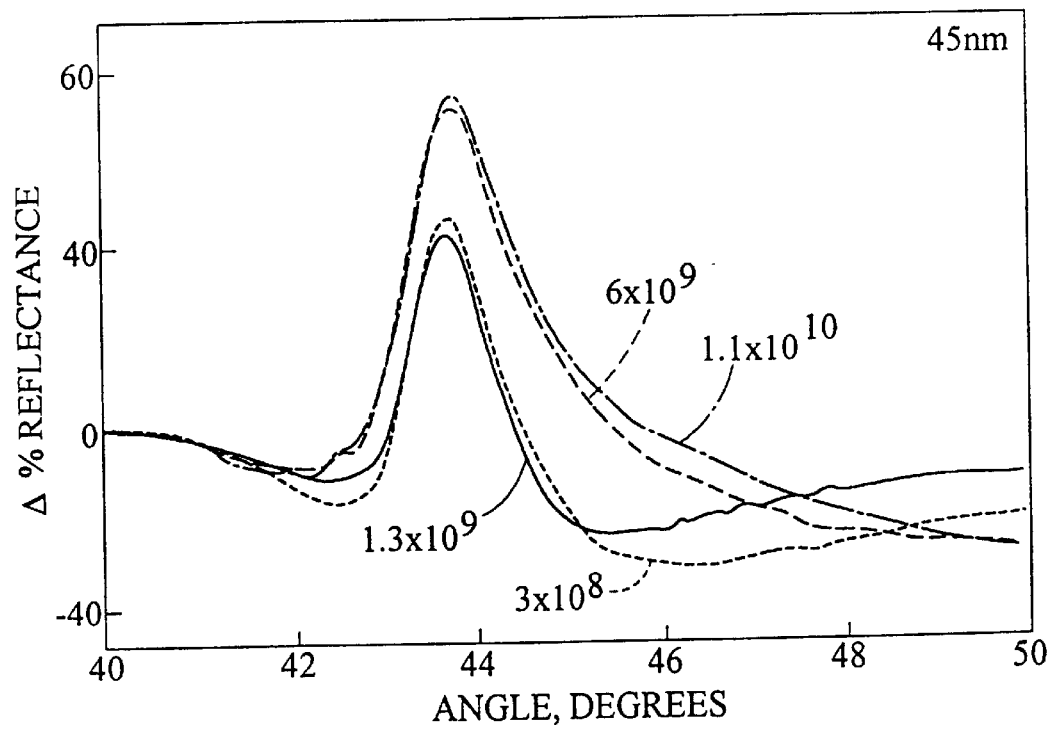

In preferred embodiments, the selected angle at which to measure reflectance is the angle at which the maximum reflectance change occurs upon binding of the colloidal Au nanoparticle to the Au film. The maximum reflectance change can be determined by taking the difference between the SPR profiles of the Au-colloid-modified film and the unmodified film. FIG. 4 shows the difference profiles calculated from the data shown in FIG. 3. For both the 35 nm diameter particles. (FIG. 4A) and 45 nm diameter particles (FIG. 4B), the maximum increase in reflectance is observed at 43.7°. This result suggests that the minimum of the SPR profile for the unmodified film is the optimal observation angle for the Au-colloid-modified film. The large size of reflectance changes observed here suggests that much lower surface concentrations may be detectable. Indeed, for 45 nm diameter particles, a number density of $1.3\times10^9$ particles/cm$^2$ results in a reflectance change of 40%. Because current scanning SPR instrumentation is able to detect a change in reflectance of <0.1%, it is possible to detect a 400-fold lower surface coverage ($3\times10^6$ particles/cm$^2$, equivalent to 0.0065% of a monolayer), assuming a linear SPR response at low coverage.

Figure 5:
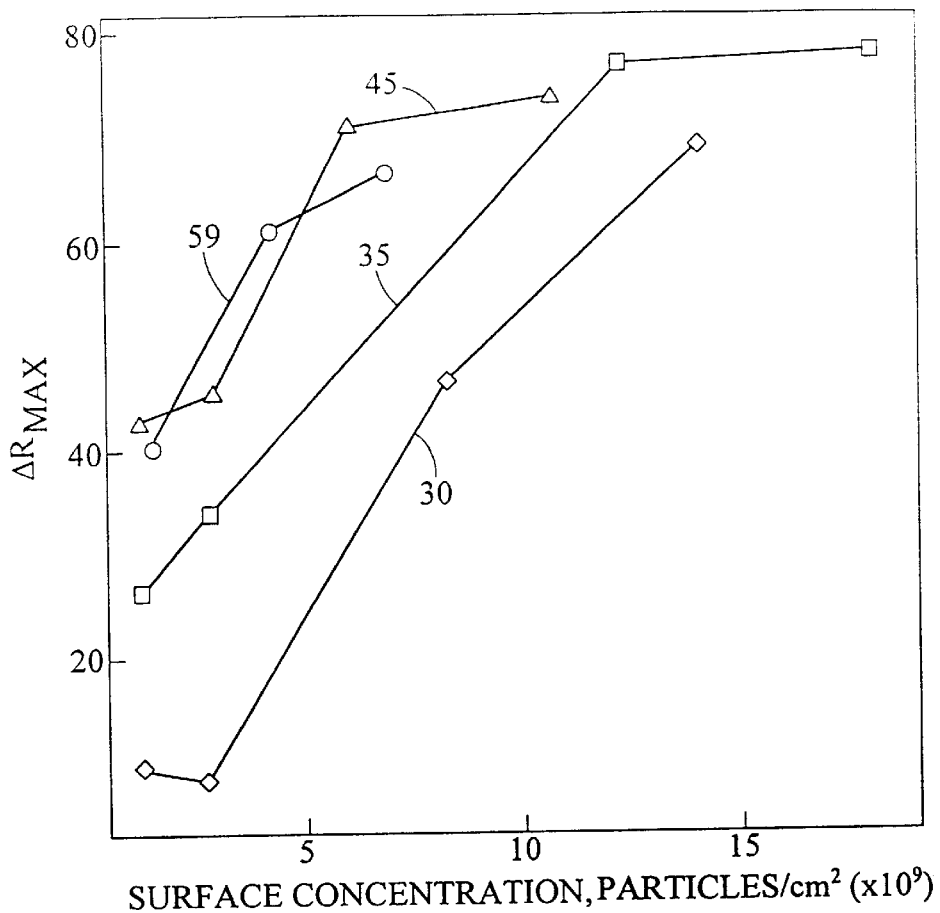
FIG. 5 plots the maximum change in reflectance as a function of number density for colloidal Au nanoparticles 30 nm–59 nm in diameter.

In FIG. 5, the maximum change in reflectance is plotted as a function of number density for the 30 nm, 35 nm, 45 nm, and 59 nm diameter colloidal Au particles. For all particle diameters, the peak of the differential profile is approximately 43.7°, again indicating that the ideal observation angle is the same, independent of particle size. In terms of assay and sensing applications, this is a distinct advantage of particle enhancement, as the angle where the largest signal will be observed can be known prior to performing an assay. This may, in some cases, eliminate the need for high-resolution scanning in order to determine the amount of immobilized material. Measurement of the percent reflectance at a specific angle may also be subject to less error, as determination of the absolute plasmon angle becomes difficult at higher surface coverage.

It should be noted that while the focus of this invention is on SPR, with other analytical techniques used to assist in characterization, the other techniques themselves can provide sensitive DNA detection. Thus, in the absence of significant non-specific particle binding, single nanoparticles are easily visualized by atomic force microscopy, field emission scanning electron microscopy, or by near field scanning optical microscopy. If the required detection limits for DNA are not achieved by SPR, other techniques can be utilized.

Biosensing Assay Formats.

One assay format that can be readily used with the methods of the invention is the "sandwich" assay, well-known in the art. Sandwich assays are generally organized in the following way: Ligand A, immobilized on a solid support, can bind to target analyte B, which can simultaneously bind ligand C. When put into contact, a complex is formed on the solid support between A, B, and C. If ligand C is labeled with a detectable "tag" then the amount of target analyte B can be quantified by measuring the signal of the detectable tag present on the solid support. It will be appreciated that there can be many variations on this basic scheme. The "target analyte" is any analyte that is the subject of an assay; preferred targets of the invention are biomolecules, including but not limited to nucleic acids, proteins, hormones, sugars, and metabolites. The "ligand" is any species capable of binding to a target; preferred ligands of the instant invention include, but are not limited to, antibodies and nucleic acids. The sandwich assay configuration is commonly used in immunoassays where the "ligands" are antibodies directed toward the target analyte.

Figure 6:
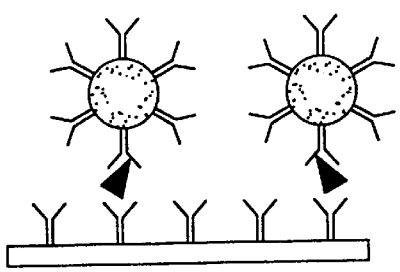
FIG. 6 illustrates schematically an example of a sandwich immunosensing assay.

FIG. 6 illustrates an example of the sandwich format in which a first antibody against an antigen is immobilized on the surface of the Au film. A second antibody against the antigen is conjugated to colloidal Au nanoparticles. When brought into contact, a complex is formed on the solid support between the first antibody, the antigen, and the second antibody conjugated to a colloidal Au nanoparticle.

Figure 7A:
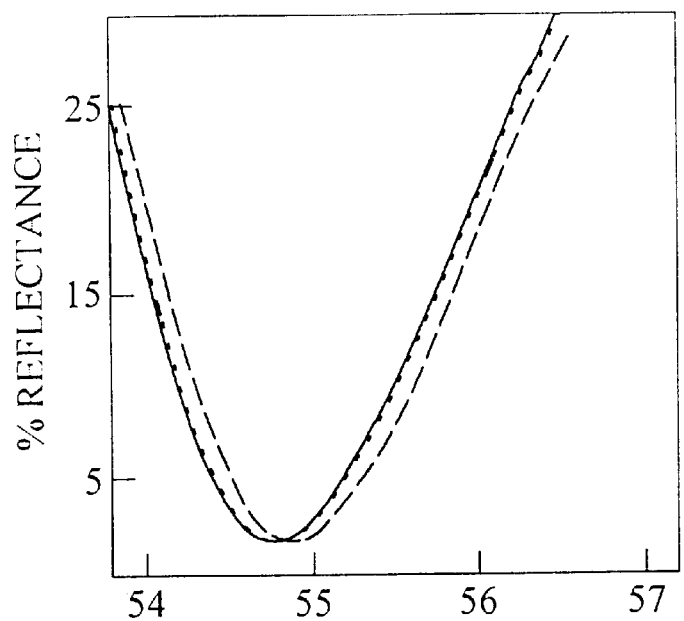
FIGS. 7A and 7B illustrate sandwich immunoassay SPR profiles obtained using an unconjugated secondary antibody (FIG. 7A) and a secondary antibody conjugated to colloidal Au nanoparticles.
Figure 7B:
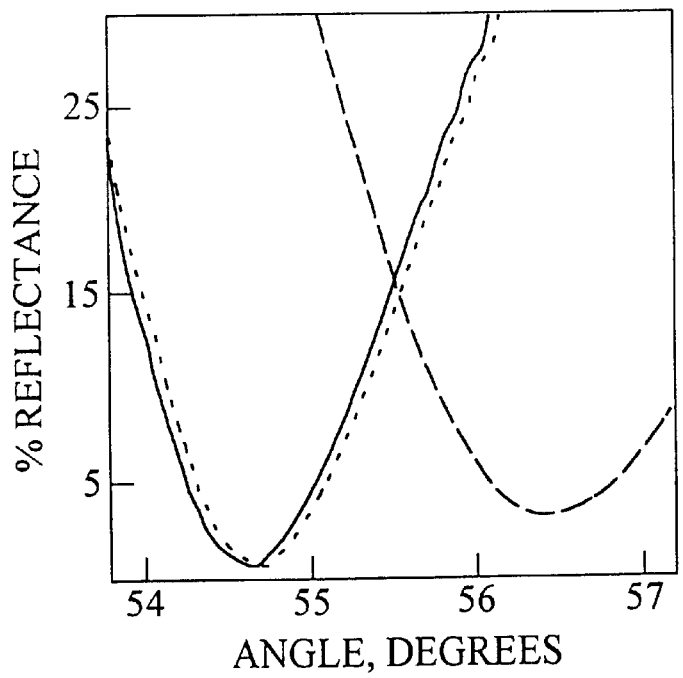

FIG. 7 shows data from an assay with the format shown in FIG. 6 using a planar SPR substrate (i.e., comprising a conductive film without an overlying matrix). To obtain this data, a 50 nm thick Au film was first modified with 3-mercaptopropionic acid (MPA), thereby forming a carboxylate terminated self-assembled monolayer (SAM). The SPR profile obtained from this modified film alone is shown by the solid line trace in FIG. 7A. Then, γ-chain-specific monoclonal goat anti-human IgG antibody [a-h-IgG (γ)] (the "first antibody" or "the primary antibody") was coupled to the carboxylated monolayer via carbodiimide coupling to free amine moieties on the antibody. Incubation of the modified film with a 0.09 mg/mL solution of human IgG [h-IgG; 150 kD] (the "target antigen") produced only a 0.04° shift in the plasmon angle. This is illustrated by the dotted line trace in FIG. 7A. Indeed, the SPR profile in the presence of the antigen, h-IgG, is almost superimposed over the SPR profile obtained from the modified film alone because the plasmon angle shift is so small. Further exposure of this film to a 8.4 mg/ml solution of $F_c$ specific monoclonal goat anti-Human immunoglobulin G antibody [a-h-IgG($F_c$)] (the "second antibody" or the "secondary antibody"), results in only a small (0.06°) plasmon angle shift. This is illustrated by the dashed line trace in FIG. 7A. However, when the secondary antibody is present as an electrostatic conjugate with 10-nm-diameter Au particle [a-h-IgG($F_c$)-Au], a 1.7° shift in plasmon angle is observed, accompanied by a 2% increase in minimum reflectance and a noticeable broadening of the SPR profile. This is illustrated by the dashed line trace in FIG. 7B. This colloid-induced 1.7° shift is 28 times larger than that observed for the unamplified assay using the same planar substrate (i.e., the 0.06° as shown in the dashed line trace in FIG. 7A). Thus, a significant increase in sensitivity is afforded through the use of protein-Au colloid conjugates in this biosensing embodiment. Biochemical specificity is also maximized under these conditions—surfaces modified with a-h-IgG(γ) show little or no reactivity with human serum (minus IgG), human immunoglobulin A, and [a-h-IgG($F_c$)-Au]. The a-h-IgG(γ)-h-IgG modified surface is also highly specific, as exposure to a conjugate of 10 nm-diameter Au with goat anti-human immunoglobulin GI (a-hIgGl-Au) leads to only a small (0.08°) plasmon shift. A more complete discussion of the materials and methods used in this immunoassay are provided in Example 2.

As mentioned previously, in preferred embodiments the assay is performed by measuring reflectance changes in the SPR substrate at a predetermined angle of incidence. The optimal angle is the one at which the largest change in reflectance is observed upon the occurrence of the biological event being detected. In the sandwich assay, this biological event is the formation of the primary antibody-antigen-secondary antibody "sandwich." To determine the optimal angle, a differential SPR profile (change in reflectance against the angle of incidence) is prepared by calculating the difference between the SPR profiles obtained for the secondary antibody and antigen steps. The peak of the differential profile occurs at the largest difference between the two spectra and thus represents the optimal angle for monitoring reflectance changes during that reaction.

Figure 8:
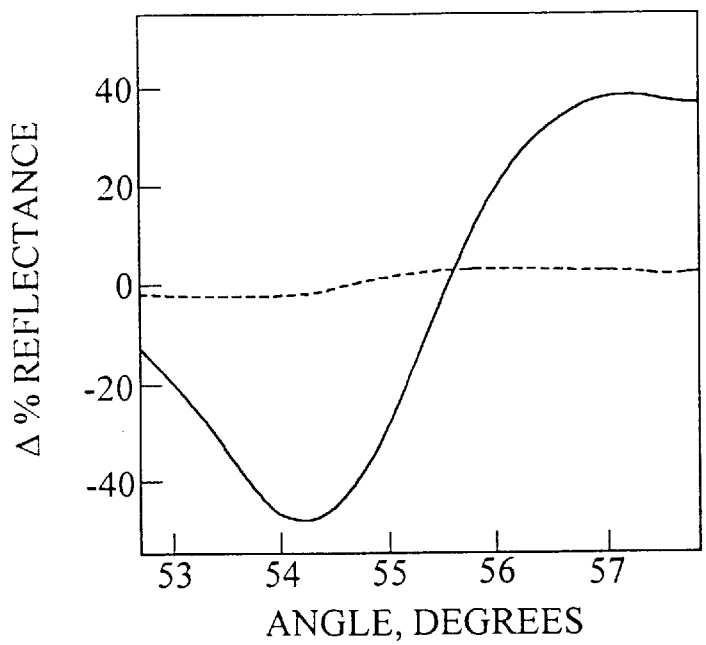
FIG. 8 illustrates a differential SPR profile ($\Delta\%$ reflectance versus angle of incidence) for the data presented in FIG. 7.

FIG. 8 represents a differential SPR profile for the data provided in FIG. 7. For the case of the addition of a-h-IgG ($F_c$), a maximum decrease in reflectance of only about 2% is obtained at an angle of incidence of 54.3° (dashed line trace in FIG. 8). By contrast, for the addition of a-h-IgG ($F_c$)-Au, a ~50% decrease in reflectance is observed at the same angle of incidence (solid line trace in FIG. 8). Thus, the use of 10 nm Au-conjugated secondary antibody leads to a 25-fold increase in sensitivity relative to unconjugated secondary antibody.

Figure 9:
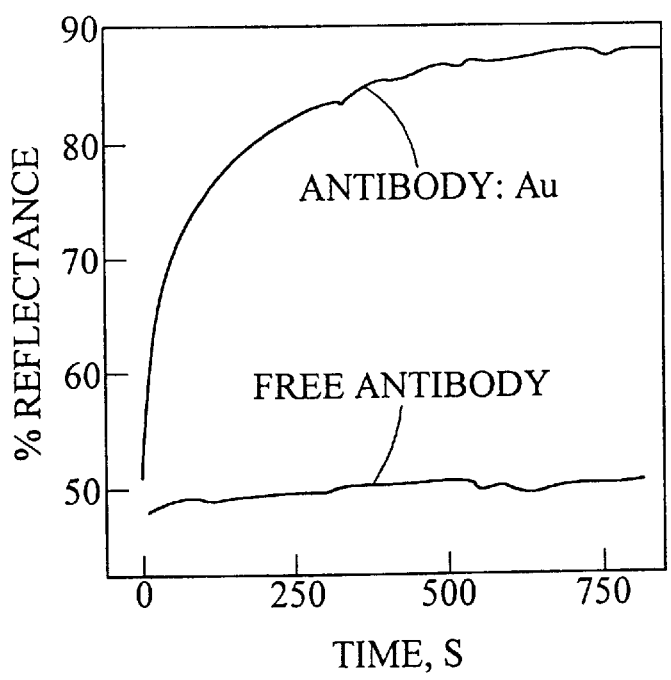
FIG. 9 illustrates reflectance time courses for the immobilization of both the unconjugated and the Au-conjugated secondary antibodies.

FIG. 9 shows reflectance time courses for the immobilization of both the unconjugated and Au-conjugated secondary antibodies. When the reaction is monitored at an angle smaller than the plasmon angle (53.4°, 50% reflectance), a change in reflectance of >40% is observed in the case of the Au-conjugated secondary antibody (trace marked "Antibody:Au" in FIG. 9), while immobilization of the unconjugated antibody to an identically prepared surface results in less than a <2% reflectance change (trace marked "Free Antibody" in FIG. 9). This illustrates the sensitivity enhancement in assays that rely on the real-time monitoring of biospecific interactions. It should be noted that this enhancement is obtained despite the protein-Au conjugate being more than 6 orders of magnitude more dilute than the free antibody (17 nM vs 56 mM).

Figure 10A:
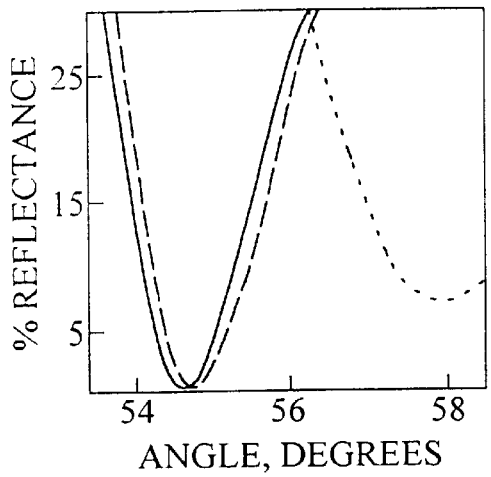
FIGS. 10A–10D illustrate the variation in colloidal Au induced plasmon shift at varying concentrations of target analyte in an immunosensing assay.
Figure 10B:
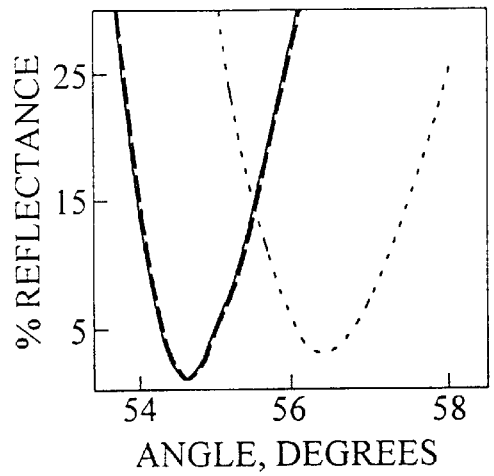
Figure 10C:
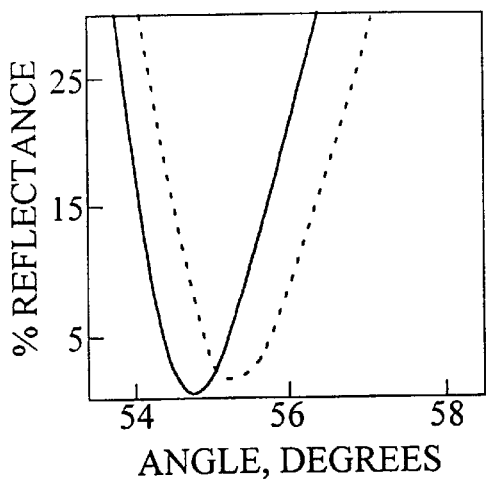
Figure 10D:
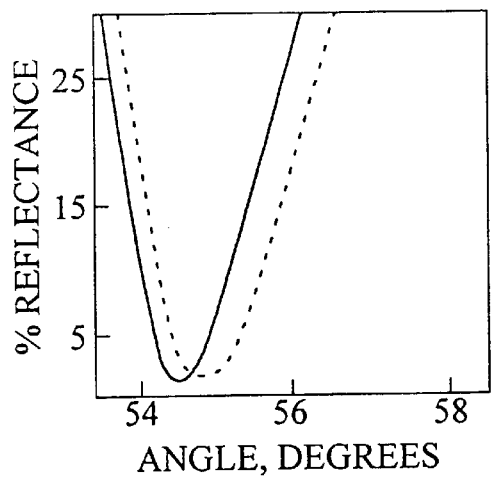

The utility of the particle enhancement methodology of the instant invention becomes most striking at low concentrations of antigen. FIG. 10 illustrates the variation of the colloidal Au-induced plasmon angle shift as a function of h-IgG concentration. The h-IgG concentrations used are 3 mM (FIG. 10A), 0.3 mM (FIG. 10B), 3.0 nM (FIG. 10C) and 6.7 pM (FIG. 10D). In each figure, the solid line represents the SPR profile for the a-h-IgG(γ) modified film; the dashed line represents the SPR profile of the a-h-IgG(γ) modified film in the presence of h-IgG only; the dotted line trace represents the a-h-IgG(γ) modified film in the presence of both h-IgG and a-h-IgG($F_c$)-Au. As expected, the observed plasmon shifts decrease as the solution antigen concentration is varied over nearly six decades (3.0 μM to 6.7 pM). The lowest h-IgG antigen concentrations—3.0 nM (FIG. 10C) and 6.7 pM (FIG. 10D)—induces SPR changes that are not detectable in the absence of a-h-IgG($F_c$)-Au. Despite these low antigen concentrations, significant shifts due to particle immobilization are still evident when the 10 nm Au-conjugated secondary antibody is used. Even at the lowest concentration of h-IgG investigated (6.7 pM=1.0 ng/ml), an easily detectable shift of 0.33° results (FIG. 10D). The ease with which this shift may be resolved reveals that the actual detection limits for 10 nm Au conjugated secondary antibody are lower than even the picomolar range.

The immunosensing embodiments described above all use planar SPR substrates (i.e., Au films modified with a monolayer of a bifunctional organic linker to which the primary antibody becomes covalently bound). As discussed in the Background of the Invention, commercially available SPR assays typically use a Au film coated with an extended (e.g., 200–400 nm thick) carboxylated dextran matrix to concentrate capture molecules, such as primary antibodies. Molecules to be localized to the film surface (e.g., primary antibodies) are covalently bound by the dextran matrix, resulting in the formation of a three-dimensional array of molecules extending ~200 nm away from the surface. There are numerous drawbacks to using such a matrix, as outlined in the Background of the Invention. The methods of the instant invention dramatically surpass the sensitivity of such prior art matrices. For example, using 10 nm Au-conjugated secondary antibody on a planar SPR substrate leads to a 3,000 fold enhancement in detection limit relative to the same assay performed in dextran matrices using unconjugated secondary antibody.

In some embodiments of the invention, even further enhancements are obtained by using colloidal Au nanoparticles that are greater than 10 nm in diameter. For example, if the immunoassays described above are performed using 41 nm Au-conjugated secondary antibodies and a planar SPR substrate, then a 30-fold amplification in sensitivity is obtained over the same assay using 11 nm Au-conjugated secondary antibodies. Compared to conventional SPR assays using dextran matrices, this represents a 100,000 fold increase in sensitivity. Indeed, using 41 nm Au-conjugated secondary antibodies and a planar SPR substrate, it is possible to detect h-IgG at a concentration as low as 10 pg/ml.

In some embodiments of the invention, conventional dextran-based matrices may be used as the substrates for colloidal Au-enhanced SPR sensing. However, depending on the matrix pore size, colloidal Au particles of the sizes used above may be excluded from the interior of the matrix by steric hindrance. A different methodology is required for such embodiments: colloidal Au nanoparticles small enough to enter the matrix are used and then, after their entry into the matrix, they are selectively enlarged by the addition of a metal plating solution, such as a solution of $Au^{3+}$ and $NH_2OH$, or preferably a commercial Ag plating solution. In this way, the Au nanoparticles can be grown by the plating solution within the matrix to a size that significantly enhances the SPR response. For example, for the sandwich immunoassay described above, 1.8 nm colloidal Au can be conjugated to secondary antibodies. The resulting conjugate can diffuse into the matrix (within which primary antibodies are covalently bound), along with the target analyte to be detected. Following the creation of (primary antibody)-(target antigen)-(secondary antibody) complexes within the matrix, an Ag plating solution is passed over the film to enlarge the colloid size. Using commercial Ag plating solution, it is possible to selectively enlarge the conjugated Au nanoparticles, without nucleating new particles. In preferred embodiments, the Au film substrate upon which the dextran is overlaid is first pre-treated with a short chain alkane thiol, such as 6-mercaptohexanol, to prevent the Ag plating solution from plating Ag directly onto the Au film through holes in the dextran matrix. When this method is used to perform the h-IgG immunoassay described above, a 30-fold enhancement is obtained over the same assay performed with 41 nm Au-conjugated secondary antibody. A $10^6$-fold enhancement is obtained relative to the same dextran-based assay performed using unconjugated Au secondary antibody.

It will be appreciated that all of the aforementioned immunosensing embodiments can be adapted for the detection of any target analyte for which suitable primary and secondary antibodies are available. In addition, it will be understood that the methods described are applicable to any molecular recognition assay in which one of the participants in the molecular recognition event can be immobilized on a planar SPR substrate, and another participant can be conjugated to colloidal Au nanoparticles. For example, a receptor-ligand interaction can be assayed by immobilizing a receptor on a planar SPR substrate, and then either conjugating the ligand directly to colloidal Au, or by using a colloidal Au-conjugated antibody that can bind to the ligand. Furthermore, the methods of the invention can be used to study desorption of Au-colloid tagged reagents from the Au film, rather than interaction-driven adsorption.

The methods describe herein provide two examples of SPR based assays based on molecular recognition: (1) an assay in which one of the molecules that participates in the recognition event is immobilized on a derivatized, planar SPR Au film substrate, and another of the molecules that participate in the recognition event is conjugated to colloidal Au of size ~10–150 nm; or (2) an assay in which one of the molecules that participates in the recognition event is immobilized within a dextran matrix overlaid onto a Au film, and another of the molecules is conjugated to colloidal Au of a diameter sufficiently small to permit the conjugated reagent to diffuse into the dextran matrix; following diffusion of the conjugate into the matrix, the Au nanoparticles are enlarged by the addition of Ag plating solution. Both strategies provide unique methods of signal amplification and the better method is best determined by evaluating some general criteria. Other criteria, in addition to that presented below, will be apparent to those of skill in the art in determining the best method for a particular purpose.

Most important is the size and nature of the capture molecule (e.g., "Ligand A" or the "primary antibody") and analyte to be immobilized. Large molecules could be excluded from diffusing into the dextran; thus the most sensitive region—close to the surface—is unavailable. Likewise, if the analyte is large, diffusion to the immobilized receptor may be impossible. Dextran matrices are also impractical if a particular orientation of the capture agent is necessary for receptor binding, as is the case for DNA hybridization or membrane studies. Many protocols are known in the art to correctly orient DNA, bilayer membranes, or proteins onto a planar surface.

The concentration of the target molecule should also be considered. With respect to h-IgG, low concentrations (100 ng/ml–100 pg/ml) are well suited for the Au enhancement on a planar film with 1 1-nm diameter Au colloid; and lower concentrations require larger colloids. However, the latter species are more likely to denature (though not usually observed). Also, there is an increased possibility of multiple interactions between the protein-bound particle and the surface. In contrast, 1.8-nm diameter Au colloid conjugates offer (in most cases) a 1:1 protein to colloid ratio. This should aid in quantification and, with optimized exposure time to the Ag plating solution, should afford detection at very low concentrations (<100 pg/ml). However, after Ag plating, further immunochemical manipulations are impossible. Finally, it should be noted that both surfaces are amenable to regeneration using standard techniques.

Greater changes in the SPR angle shift are expected for particles able to couple more efficiently to the surface plasmons in the Au film. Thus, one embodiment of the invention is directed to generating particles with tunable absorbance spectra for use as SPR tags. Absorbance of light by Au nanoparticles leads to excitation of particle-based surface plasmons, an effect that is size dependent. Thus, one simple means of tuning the absorbance spectrum for SPR tags is to use different sizes of Au nanoparticles. Two of the problems traditionally associated with larger colloidal Au nanoparticles (i.e., those with diameters greater than 35 nm) have been polydispersity and instability (relative to smaller particles). Since it is known that the stability of colloidal particles decreases with increasing size, it follows that part of the instability problem could be solved through improved monodispersity. Moreover, for applications in which the Au nanoparticles are reagents, it is essential to have "reagent-grade" (i.e., relatively pure) materials.

While it is easy to understand that larger changes in reflectivity are observed for larger particles (presumably due to both the scattering and greater changes in the dielectric associated with the binding of more Au metal per particle), significant changes were not expected for the very small molecular Au clusters. Although smaller particles give less dramatic shifts than are observed for larger Au tags, their smaller "footprint" allows a higher degree of labeling on the surface, and makes it easier to arrange for single particle binding events to correspond to single biological binding events. An added advantage of decreased particle tag size is improved diffusion of the tagged biomolecule.

Another example of the utility of colloidal Au reagents in biochemical SPR experiments involves binding and displacement of a colloidal Au-tagged protein. In an example of this embodiment of the invention, anti-biotin was covalently bound to a planar SPR substrate. Introduction of biotinylated colloidal Au (prepared by adsorption of biotinylated BSA to 10-nm Au) leads to a small change in reflectivity indicative of a low coverage of conjugate, which is in turn indicative of a small amount of active anti-biotin on the surface. When the antibody: antigen-Au complex is exposed to a high concentration of biocytin, a water-soluble analogue of biotin that binds to anti-biotin, the colloidal Au tagged biotin is displaced, and the SPR reflectivity returns to its original position. These experiments show that binding of colloidal Au conjugates to SPR surfaces is reversible, and thus allows the use of SPR to detect binding of low MW species by ligand displacement.

Figure 15A:
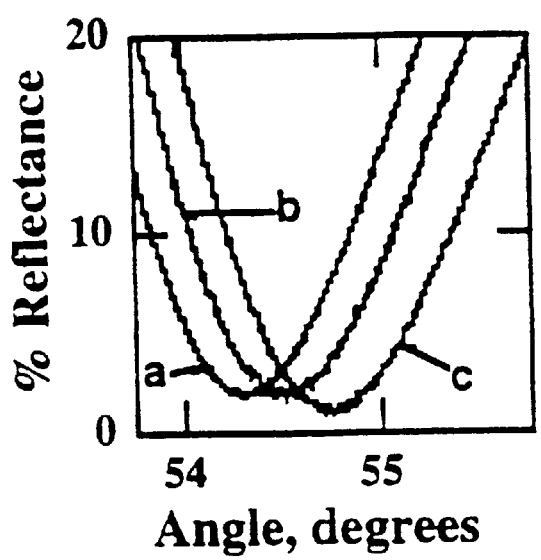
FIG. 15A shows the SPR minimum for the following modifications on a mixed SAM (90% 11-mercapto-1-undecanol:10% 16-mercaptohexadecanoic acid) on Au: electrostatically immobilized protein A/anti-IL-5 complex (a); 0.6 ng/mL IL-5/25 mg/mL HSA (b); IL-5:Au (with 0.5% Blotto Blocker) (c).
Figure 15B:
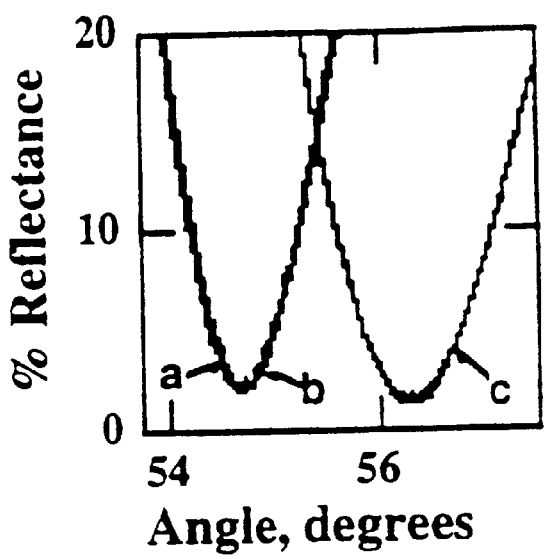
FIG. 15B shows the SPR minimum in a similar experiment, but with 600 ng/mL IL-5/25 mg/mL HSA introduced.

Having shown that Au-particle amplification can lead to very large improvements in the sensitivity of SPR using standard IgG immunoassays as a model system, this technique has been applied to several other systems, e.g., to detection of biologically-important soluble factors in blood serum; for example, the cytokine interleukin-5 (IL-5). IL-5 is produced by T-lymphocytes and appears to be the main cytokine involved in the control of eosinophilia. Since eosinophils are important in allergy, IL-5 is thought to be of key importance in the development of allergic diseases (e.g., asthma). The pharmacological importance of IL-5 and other cytokines makes these molecules good targets for biosensing. The selectivity of IL-5:Au conjugate to protein A/anti-IL-5 on an Au film is shown in FIG. 15. The observed angle shift was far greater for the specific interaction than for a nonspecific interaction (ST4:Au conjugate). There was a small amount (0.1°) of non-specific binding with ST4:Au. The specific interaction shifted the minimum 1.6°. (0.5% Blotto was used in these experiments to inhibit nonspecific binding). While this experiment illustrates both the sensitivity of Au-amplification and the selectivity of this assay, biological samples will contain free cytokines, not cytokine:Au conjugate. To detect IL-5 in such samples, a pseudo-competitive assay may be used. In this experiment, the protein A/anti-IL-5 coated Au film is exposed first to free IL-5 in the presence of a high concentration of human serum albumin, to mimic serum. After collection of the SPR curve, the surface is exposed to IL-5:Au conjugate. Due to the slow dissociation kinetics for anti-IL-5/1 L-5 interaction, little if any IL-5 is displaced from the surface upon exposure to conjugate, but rather that IL-5:Au binds only to "open" antibody on the surface. Thus, the amount of angle shift resulting from exposure to conjugate is inversely proportional to the amount of analyte in the initial ("serum") sample.

Figure 11A:
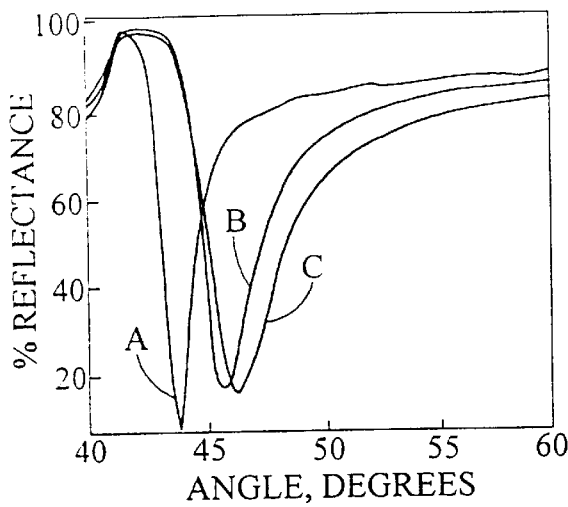
FIGS. 11A–11C illustrate the progressive enhancements in SPR response that occur when a Au film is coated with a 15 nm (FIG. 11A), 24 nm (FIG. 11B), and 33 nm (FIG. 11C) thick layer of SiO$_2$ and then has 12 nm colloidal Au adsorbed thereon.
Figure 11B:
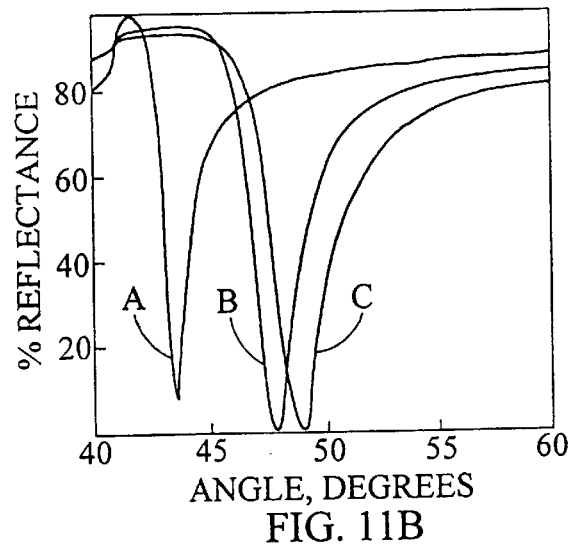
Figure 11C:
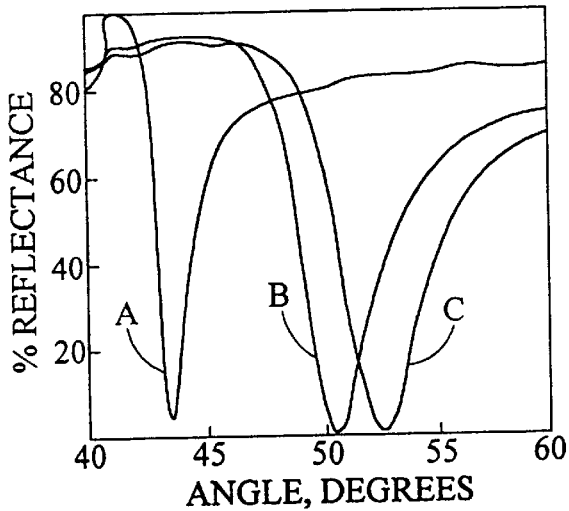

In preferred embodiments of the invention, even further enhancements of the colloidal Au-conjugated SPR response are obtained by optimizing the coupling distance between the Au nanoparticles and the Au film. In some embodiments, an inorganic spacer, preferably $SiO_2$ deposited through thermal evaporation, is placed over the surface of a Au film to increase the distance between the colloidal Au and the Au film. In other embodiments, optimization of the coupling distance is achieved by overlaying the Au film with one or more polymer layers, preferably polystyrene sulfonate and/ or polyalylamine hydrochloride built up through electrostatic interactions. In an especially preferred embodiments, a 30–40 nm thick layer of $SiO_2$ is used in conjunction with 12 nm colloidal Au. FIG. 11 illustrates the progressive enhancements in SPR response that occur when a Au film is coated with a 15 nm (FIG. 11A), 24 nm (FIG. 11B), and 33 nm (FIG. 11C) thick layer of $SiO_2$ and then has 12 nm colloidal Au adsorbed thereon. In each figure, trace A is the SPR profile of the Au film without the $SiO_2$ layer or localized Au colloid; trace B is the SPR profile of the Au film with the $SiO_2$ layer only; trace C is the SPR profile of the Au film with the $SiO_2$ layer and Au colloid attached. It is understood that the thickness of a spacer overlayer producing a maximum shift for a certain amount of immobilized colloid depends on (i) the thickness of the Au film; (ii) the composition of the film (different results would be obtained for Ag films, for example); (iii) the excitation wavelength; (iii) the size of the colloidal Au particles; (iv) the composition of the colloid (different results would be obtained for colloidal Ag, for example); and (v) the surface coverage. In addition, it will be understood that there are many other materials that can be suitable spacers, including but not limited to, metal oxides, sulfides, nitrides, or any other material that contains metal ions in a positive oxidation state.

For $SiO_2$ overlayers, a 30 nm thickness improves sensitivity 3-fold. Similar results have been observed for polymeric spacer layers composed of alternating cationic and anionic polymers. Not only does this development lead to improved detection limits, it also opens up all the attachment chemistries used on glass surfaces, and can improve film stability.

The $SiO_2$ coating, while thin and certainly somewhat porous, also serves to protect the underlying metal from chemical attack. While reactivity is not a concern for Au films, oxidation can prevent the use of Ag metal for SPR. Ag films are known to have sharper angle-dependent reflectivity curves, and could be a better choice of substrate if not for their rapid oxidation.

It is an important aspect of the present invention that the distance of the colloidal nanoparticle from the metal film can be essentially measured by the SPR detection. Because of this property, it is not necessary that assays being conducted on the film surface require the presence or absence of the colloidal nanoparticle. Rather, according to the present invention, it is possible to conduct an assay whereby the presence of an analyte acts to increase or decrease the distance of the colloidal nanoparticle from the metal film surface.

Preferred embodiments of the invention use colloidal Au nanoparticles to enhance the SPR profile of metal SPR substrates. However, it is to be understood that the metal nanoparticles can be comprised of other materials with complex indices of refraction, including but not limited to Ag, Cu, Al, or alloys comprised of two or more of Au, Al, Ag, and Cu. In other embodiments, the metal nanoparticles comprise a core of Ag, Al, Au, or Cu (or an alloy of two or more of these metals) substantially covered by a shell of any metal, any oxide, any sulfide, any phosphide, or any organic or inorganic polymer. In addition, although preferred embodiments employ metal nanoparticles that are substantially spherical, it is to be understood that other shapes are also contemplated.

Figure 16:
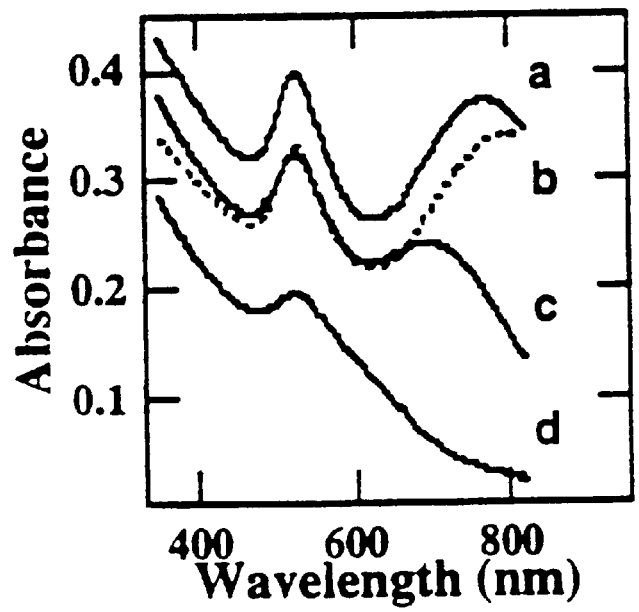
FIG. 16 shows the UV-Vis optical spectra of colloidal dispersions made by mixing $Na_2O_3$ with HavCly in different ratios: (a) 1.3:1, (b) 1.2:1, (c) 1.4:1, and (d) 2.0:1.

A wide range of wavelength "tunability" is possible for AuS core/Au shell particles, which have been described by the groups of Haus and Halas. See, e.g., Averitt et al., Phys. Rev. Lett. 78:4217–4220 (1997). By varying the preparation conditions, it is possible to tune the position of the second $\lambda_{max}$, indicative of a control of the ratio of core to shell size. FIG. 16 shows optical spectra for several batches of these particles. Particles having significant absorbance at 632 nm are particularly useful, as that is the laser wavelength most commonly employed in SPR work. Strong absorbance of light at the wavelength of the surface plasmon results in a high degree of film-nanoparticle coupling, which in turn leads to large SPR response and increased sensitivity.

Polydispersity in particle preparations leads to difficulties in interpreting SPR data, as amplification is a function of particle size. Synthesis of AuS/Au shell particles by methods analogous to those used for colloidal Au (i.e., rigorous cleanliness, ultrafiltered solvents, rapid reagent addition, rapid stirring and reflux) leads to marked improvement in monodispersity. Quantitative measurement of extinction coefficients are made on the resulting AuS/Au particles, both in solution and on surfaces. On surfaces, particle coverage is unambiguously established by AFM and FE-SEM. In solution, S and Au atomic absorption is carried out on a sample of the as-prepared sol in which all particles have been removed by aggregation/centrifugation. This permits determination of whether 100% of the added Au was converted to dispersible particles. Subsequently, a combination of TEM image analysis and static light scattering is used to establish mean particle size and dispersity. These numbers can in turn be used to calculate a particle concentration in solution. For both sets of measurements, the observed data may be correlated to theory using Bohren's program for calculation of core- shell absorption and scattering.

To determine the optimal conditions for core/shell particles in ultrasensitive SPR applications, SPR spectra is collected at multiple wavelengths, and the results compared with expected behavior based on optical spectra for the particles. Of course at each wavelength, a different Au film thickness and different collection angle may be optimal; the relationships between these parameters are given by the Fresnel equations, and can be modeled very efficiently using available software.

Ultrasensitive SPR detection of DNA hybridization.

In certain preferred embodiments, the colloidal Au enhancement methods of the instant invention are used to detect DNA hybridization. In one embodiment of the invention, a solution suspected of containing a target DNA sequence is treated with reagents that conjugate colloidal Au to nucleic acids within the solution. Following conjugation, the solution of nucleic acids is contacted with a planar SPR Au film substrate that has been modified with an oligonucleotide probe having sequence complementary to the target DNA sequence. If the target is present, it will hybridize to the immobilized probe, thereby bringing colloidal Au to the surface of the Au film. The resulting change in the SPR response of the film can be monitored to detect the presence of the target. Methods for the attachment of nucleic acids to metal films are well known in the art. For example, amine modified nucleic acids can be attached to a 16-mercaptohexadecanoic acid-derivatized surface via 1-ethyl-3-(3-dimethylaminopropyl) carboiimide/N-hydroxysulfosuccinimide crosslinking to carboxylate groups. Methods for DNA attachment to Au films are provided in Herne et al., J. Am. Chem. Soc. 119: 8916–8920 (1997), incorporated herein by reference in its entirety.

Figure 12:
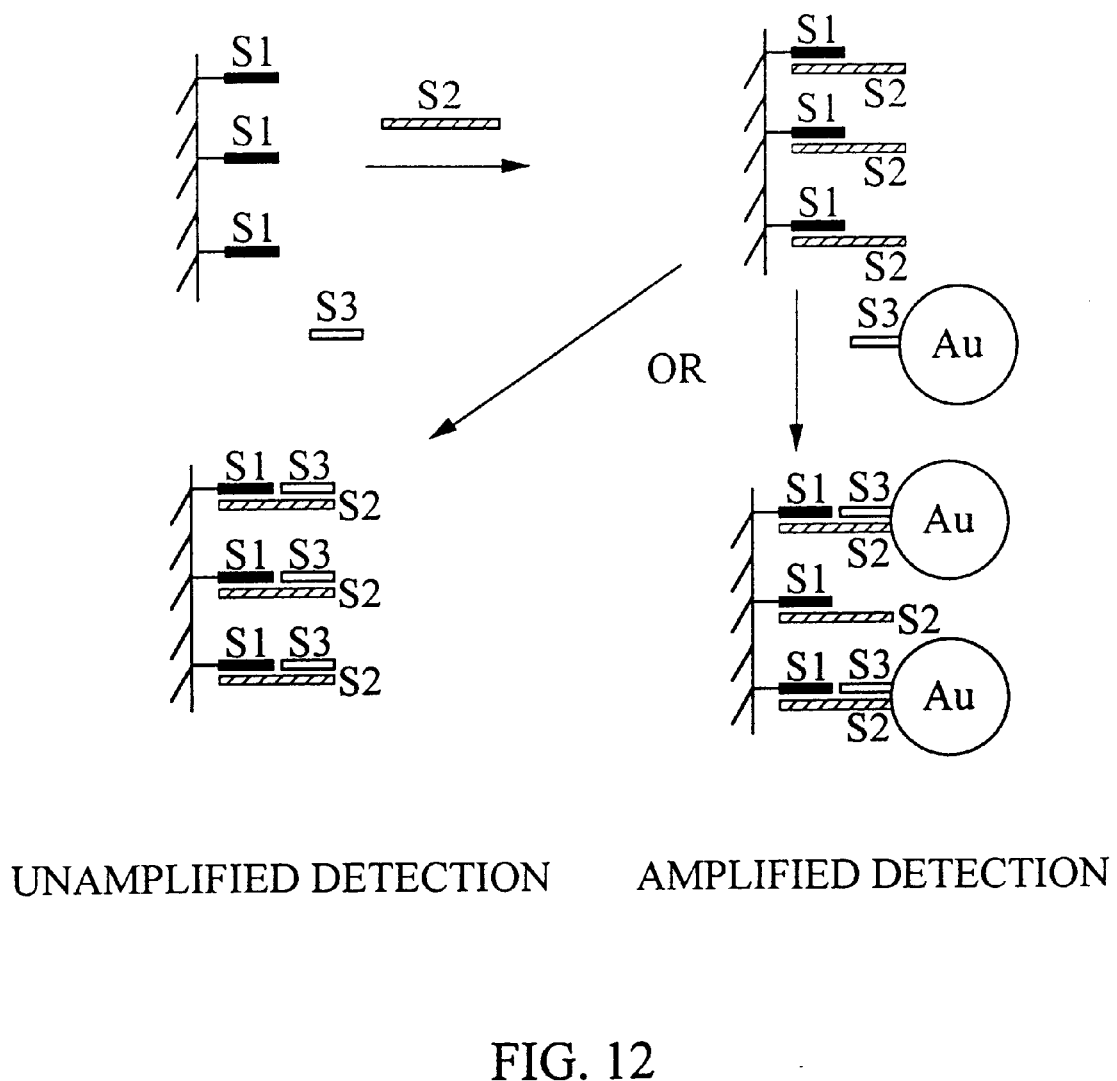
FIG. 12 illustrates schematically an example of a nucleic acid hybridization assay.

In some preferred embodiments, a "sandwich assay"-type hybridization format is used for DNA detection; an example is illustrated schematically in FIG. 12. In this example, an oligonucleotide probe (S1) which has a sequence complementary to a first portion of the target DNA sequence (S2) is immobilized on the surface of a planar SPR substrate. The SPR substrate is then contacted with a solution suspected of containing the target DNA sequence (S2), and also with a colloidal Au-conjugated oligonucleotide (S3:Au) having a sequence complementary to a second portion of the target sequence. The sequences of S1 and S3:Au are designed such that in the presence of the target (S2), the sequences S1, S2 and S3:Au form a tripartite hybridization complex. In this way, colloidal Au is brought to the surface of the Au film only if the target sequence (S2) is present. The resulting changes in the SPR response of the film can be monitored in order to detect the presence of the target sequence.

The colloidal Au can be conjugated to the oligonucleotide (S3) by any of a number of methods known in the art. For example, thiol labeled DNA can be prepared, and the thiol group can serve to couple the DNA to Au as described in Mirkin et al., Nature 382: 607–609 (1996), Elghanian et al., Science 277: 1078–1081 (1997), Storhoff et al., J. Am. Chem. Soc. 120: 1959–1964 (1998), Storhoff and Mirkin, Chem. Rev. 99:1849–1862 (1999), and Mucic et al., J. Am. Chem. Soc. 120: 12674–12675 (1998), each of which is incorporated herein by reference in its entirety. Alternatively, biotinylated DNA can be prepared, and then conjugated to streptavidin: Au conjugate. Example 3 provides a detailed protocol for the preparation of such conjugates. In some embodiments, the SPR substrate is treated with mercaptohexanol which helps the immobilized probe DNA to "stand up" by decreasing physisorption.

Figure 13:
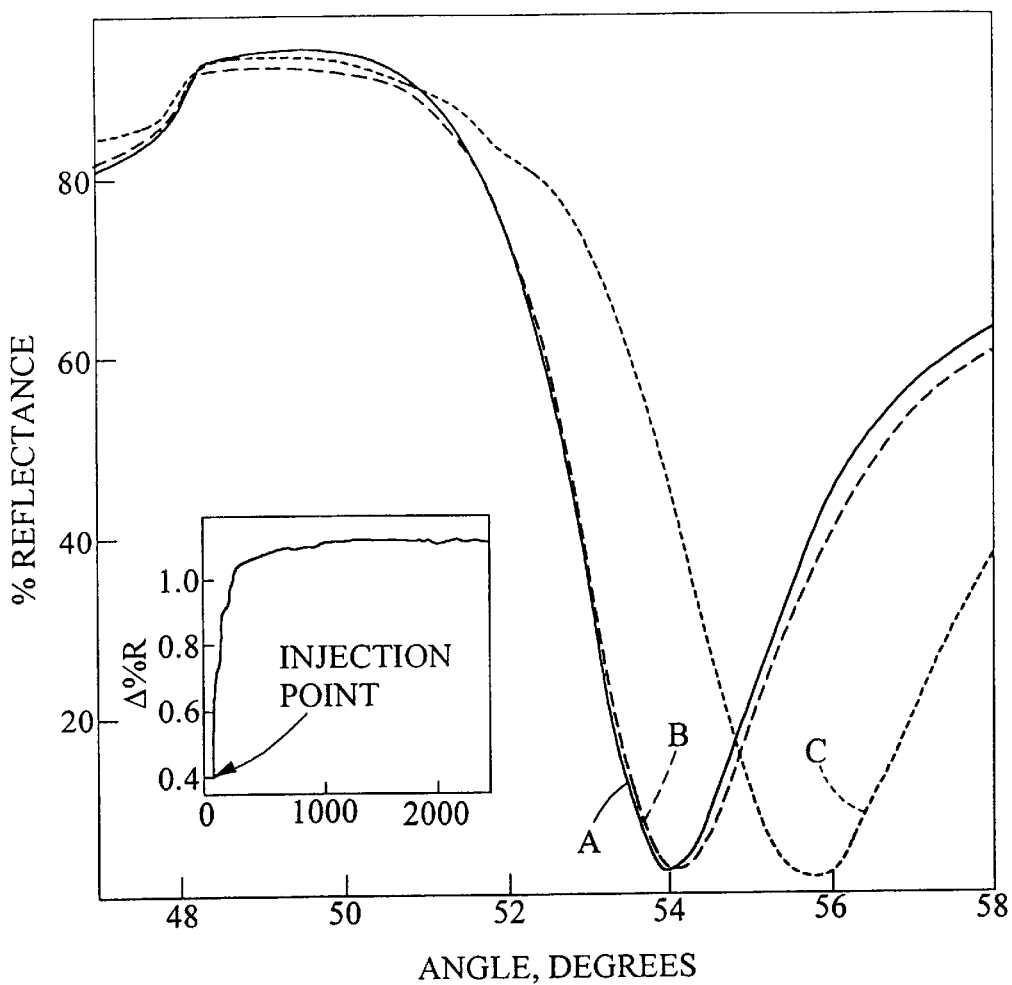
FIG. 13 illustrates an SPR profile for a nucleic acid hybridization assay conducted using the scheme in FIG. 12.

FIG. 13 shows an example of an SPR profile obtained using the abovementioned assay format. In this example, the target (SEQ ID NO:2) is a 24-mer oligonucleotide. SEQ ID NO:1 and SEQ ID NO:3:Au are 12-mer probe oligonucleotides, each of which is complementary to one half of SEQ ID NO:2. SEQ ID NO:1 has a 5' amine group through which it was immobilized to the Au film as described above. SEQ ID NO:3 has a 3' thiol group to which colloidal Au is attached. SEQ ID NO:1, SEQ ID NO:2, and SEQ ID NO:3 have the following sequences:

| | |
|---|---|
| 5'-$H_2N$-$C_6H_{12}$-CGC ATT CAG GAT-3' | SEQ ID NO:1 |
| 5'-TAC GAG TTG AGA ATC CTG AAT GCG-3' | SEQ ID NO:2 |
| 5'-TCT CAA CTC GTA $C_6H_{12}$-SH-3' | SEQ ID NO:3 |

Trace A in FIG. 13 shows the SPR response of the SEQ ID NO:1 conjugated Au film in the absence of the other reagents. Trace B shows that in the absence of SEQ ID NO:3:Au, the hybridization of SEQ ID NO:1 to SEQ ID NO:2 leads to only a very small angle displacement (0.1°) for the SPR reflectivity minimum. Trace C shows that when the SEQ ID NO:3:Au conjugate is added, there is a pronounced plasmon angle shift, which corresponds to an approximately 18-fold increase in SPR response compared to what was observed in the absence of SEQ ID NO:3:Au.

In certain preferred embodiments, the Au film is overlaid with a spacer in order to optimize the coupling distance between the Au film and the colloidal Au, as described above. The preferred spacer is a layer of $SiO_2$.

It will be appreciated that application of the Au-colloid SPR enhancement methodology need not be restricted to DNA detection assays with the probe configuration described above. There are many different assay formats known in the art for the detection of specific DNA sequences that rely on two central elements: (1) an immobilized probe (or probes) complementary in sequence to a portion of the target DNA sequence of interest; and (2) a detectable tag conjugated to a molecule that becomes associated, either directly or indirectly, with the immobilized probe. It will be appreciated that the methods of the instant invention can be readily adapted by one skilled in the art to enable SPR detection of target nucleic acid sequences in any assay format that relies on these two elements. Moreover, the same methodology can be applied to configurations in which the probes and/or target consist of other nucleic acids (e.g., RNA), nucleic acid analogs (e.g., peptide nucleic acids, etc.), or a combination thereof.

One of the unique features of SPR-based assays is that binding data can be acquired in real time to monitor the progress of the reaction. The inset to FIG. 13 shows the kinetic plot of the second hybridization step (i.e., the probe:Au conjugate binding to surface-confined oligonucleotides) by monitoring the SPR reflectivity changes at a fixed incident angle, 53.2°, as a function of time. As expected, the signal changes dramatically in the first 5 minutes, with the hybridization process being nearly complete after 60 minutes.

The changes in the SPR response of the Au film can be reversed via DNA "melting" (i.e., dehybridization by heating the substrate), or by DNA digestion of the tripartite complex at a site that releases the Au nanoparticles. Again, the melting or DNA digestion can be monitored in real time to obtain kinetic data. In the case of DNA melting studies, exact changes in temperature at a metal film induced by pulsed or continuous laser irradiation can be exactly calculated. Detection of single nucleotide polymorphisms (SNPs), for which hybridization/dehybridzation thermodynamics and kinetics are highly temperature sensitive, can be achieved by monitoring the SPR response of the Au film in response to precise laser-induced temperature variations on the surface of the Au film. In the case of DNA digestion, cleavage of the surface confined oligonucleotide/probe:Au complex—either in a single or double stranded region—will be observed as a shift in the plasmon angle as the bound colloid gold is released.

As discussed above, the methods of the instant invention using scanning SPR allow the detection of less than $3 \times 10^6$ particles/cm$^2$ for 45 nm diameter Au-colloid nanoparticles. If each particle is conjugated to a nucleic acid probe as described above, it is possible to detect $3 \times 10^6$ target nucleic acid copies/cm$^2$. DNA hybridization assays are commonly performed in a microarray format using reagent spots of around 50 $\mu$m in diameter, as described in Bowtell, Nat. Genet. Suppl. 21:20–24 (1999), incorporated herein by reference in its entirety. Assuming a 50 $\mu$m spot size, this means that the Au-colloid SPR enhancement methods herein provided are capable of detecting as little as 60 copies of a target nucleic acid. Even lower levels can be expected using larger Au colloid nanoparticles >45 nm in diameter. This level of sensitivity is unprecedented in the art. The methods herein provide new opportunities for PCR-free hybridization biosensors and for DNA diagnostics in general.

Imaging SPR and Microarray Assays.

The technique of imaging SPR is used in some embodiments to monitor analyte binding to a microarray, such as a microarray of DNA probes on a Au film-based SPR substrate. In conventional scanning SPR, SPR reflectivity is measured as the angle of incidence is varied through the angular range within which SPR occurs. Hence, at each angle of incidence, a single measurement of the SPR reflectivity of the entire SPR substrate is obtained. By contrast, in imaging SPR embodiments, a fixed angle of incidence is used, and the light that undergoes total internal reflection is imaged, preferably onto the surface of a charge coupled device (CCD). The resulting image spatially depicts SPR reflectivity variations. The changes in SPR reflectivity result from localized changes in the refractive index near the surface of the SPR substrate; these latter changes in turn result from the adsorption or desorption of material at the surface of the SPR substrate. Hence, the reflectance image can reveal sites on the SPR substrate where such binding and desorption events have taken place.

In preferred embodiments, the colloidal-Au reagents described above are used as contrast agents for imaging SPR. The image is preferably captured at the angle at which the greatest increase in reflectivity is observed upon binding of colloidal-Au tagged reagents to the Au film. In the resulting image, regions of highest intensity represent areas of the Au film that have undergone the largest increases in reflectivity, and hence have bound the largest amounts of colloidal Au. As described above, the angles of maximum reflectivity change (the maximum increase and the maximum decrease in reflectivity) can be readily determined by subtracting the SPR profile of the "bare" Au film (i.e., without bound colloid) from the SPR profile obtained when colloidal Au binds to the Au film.

In preferred embodiments, the CCD camera is configured such that the "bare" Au film appears black in the reflectance image. In this way, any changes in reflectance can be readily observed above the "background" reflectance of the Au film.

In preferred embodiments, the SPR substrate is imaged at the angle of incidence at which the maximum increase in reflectance is observed upon colloidal-Au adsorption. However, it will be appreciated that the substrate can also be imaged at the angle of incidence at which the greatest decrease in reflectance is observed upon adsorption of colloidal Au.

Because imaging SPR simultaneously gives reflectance data for multiple discrete regions of the Au film, this technique enables SPR-based microarray assays to be performed. In these embodiments, reagents—such as antibodies, DNA probes, etc.—are localized to specific discrete regions of the Au film. In preferred embodiments, a different reagent is immobilized to each discrete region. Methods for the arraying of biomolecules in this manner on solid supports are well known in the art. A fluid suspected of containing targets of interest is then contacted with the Au film, along with colloidal-Au conjugated reagents as described above. The Au film is then imaged using the imaging SPR apparatus. The normalized reflectance intensity at each region on the Au film reveals the amount of target that has bound thereto; the position of the reflectance signal reveals the identity of the target. In this way, it is possible simultaneously to quantify multiple targets. Moreover, it is also possible using the methods of the invention to obtain kinetic data simultaneously for multiple targets (e.g., for DNA polymorphisms).

In some embodiments of the invention, assays are performed using mixtures of more than one size of colloidal-Au nanoparticles. Because the angle of maximum reflectance change varies with nanoparticle size, in such embodiments it is necessary to image the SPR substrate at more than one angle of incidence. For example, using a 50 nm thick Au film, a large reflectance change is observed at 70° when 10 nm colloidal Au becomes localized to the Au film, but no change is observed at this angle when 35 nm Au colloid becomes localized to the film. However, if the angle of incidence is raised to 73°, then a large reflectance increase is observed for 35 nm Au-colloid, but not for 10 nm Au-colloid. Thus, measurement at both angles may be used to determine the amount of each particle type present.

In preferred embodiments, an imaging SPR instrument is used in which the SPR substrate is oriented horizontally. This can be done by placing the prism base facing upright in the horizontal plane. The SPR substrate can then be placed on top of the prism base, and optically coupled to the prism using, for example, a drop of immersion oil. In strongly preferred embodiments, the prism is mounted on a rotational stage in order to accommodate adjustment in the incident angle.

The horizontal prism geometry provided by the instant invention allows for two significant improvements over SPR instruments used in the art. First, positioning the SPR substrate parallel to the laser table (i.e., in a horizontal, face-up orientation) allows the rapid and parallel introduction of solutions and reagents to the sample surface. Indeed, very simple experiments may be performed with all solution chemistries contained in a droplet atop the sample. Liquid reagents may also be introduced robotically in this geometry, as opposed to prior art vertical sample positioning where solution must be flowed to the substrate. Secondly, the absence of a complicated flow cell for the introduction of liquids requires only that the sample be placed atop the prism in order to acquire an image. Substrates may be rapidly interrogated in a serial fashion in this arrangement, much in the same way 96-well plates are introduced to plate readers. Accordingly, the possibility for robotic introduction of substrates is greater in this horizontal geometry than in a prior art vertical sample orientation.

Figure 14:
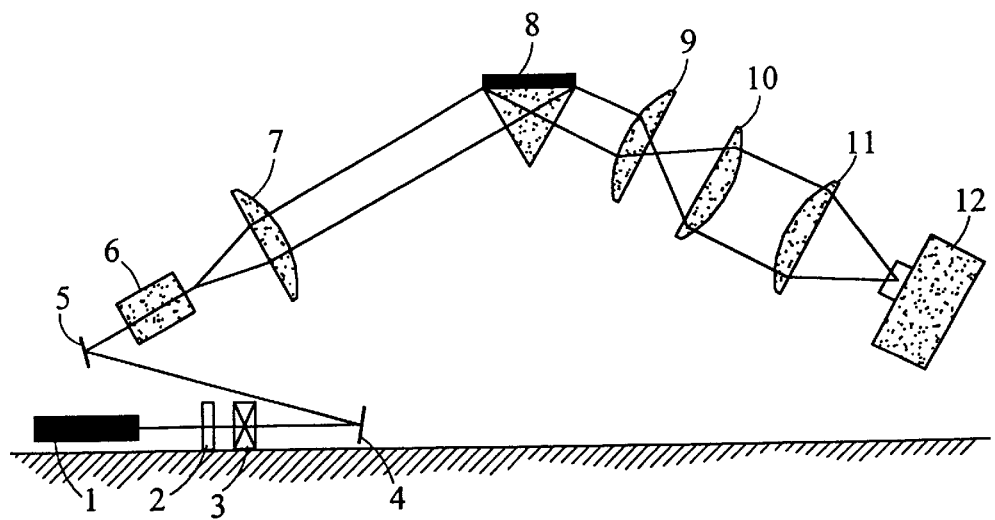
FIG. 14 illustrates schematically an example of an imaging SPR instrument provided by the instant invention.

FIG. 14 illustrates in front elevation perspective a preferred embodiment of the imaging SPR configuration outlined above. The instrument is mounted on an optical bench 13. The excitation source 1 is preferably a laser, most preferably either a 1 mW HeNe laser (632.8 nm, 500:1 polarization) or a $Ar^+/Kr^+$ laser that permits excitation at multiple wavelengths. Laser light is passed through a neutral density filter 2, and then through a linear polarizer 3 to further increase the polarization extinction. Polarization is parallel with respect to the horizontal plane and is therefore p polarized at the horizontally oriented prism/sample assembly 8. Two mirrors 4 and 5 then steer the beam upwards, preferably at a 20° angle, from the surface of optical bench 13 into a spatial filter 6. Spatial filter 6 expands the beam, at which point the center of the beam is collimated by a plano-convex lens 7. Spatial filter 6 preferably comprises a 60× microscope objective with a 5 µm pinhole, and preferably expands the beam to ~4.5 inches in diameter. Plano-convex lens 7 preferably collimates the expanded beam to 3-inches in diameter. It is important to note that this dramatic beam expansion allows illumination of the sample with a wave front that has only a very slight spatial intensity fluctuation. This avoids potential background subtraction ambiguities in the acquired images.

Collimated light leaves lens 7 and enters the prism/sample assembly 8. The 20° upward beam angle provides the 70° angle of incidence at the prism/sample assembly 8 that is optimal for high contrast SPR imaging of thin Au films. In preferred embodiments, the prism/sample assembly comprises a 70°-70°-40° prism positioned such that its base is parallel to and facing away from the optical table 13. An SPR substrate, preferably comprising a 50-nm-thick Au film evaporated onto a microscope slide, is then optically matched to the prism base with a small drop of immersion oil. Coarse positioning of the sample holder is accomplished by sliding the prism/sample assembly 8 on a vertically mounted rail, while fine pressure adjustments are made with the micrometer-actuated translation stage. Attenuated total internal reflection of the expanded beam occurs, resulting in passage of the beam downwards to the collection leg of the apparatus. At this obtuse imaging angle, the reflected beam is compressed about one dimension as indicated in FIG. 14. This is corrected by re-expanding and collimating the image with a pair of hemicylindrical plano-convex lenses 10 and 11. The beam is then refocused onto and collected by the charge coupled device (CCD) camera 12.

Because the beam is deflected upwards by mirrors 4 and 5 from the surface optical bench 13, optical elements 5 through 12 in FIG. 14 are preferably mounted on a high-stability rail system to provide a rigid structure. In preferred embodiments, mirrors 4 and 5 and the rail system can be adjusted to vary the angle of incidence and collection over the entire useful SPR range (i.e., from about 45° to about 80°).

Imaging SPR instruments are generally considered to be less sensitive than scanning SPR instruments. However, using the imaging SPR instrument and the Au-colloid (12 nm) enhancement methods of the instant invention, has allowed the reliable detection of approximately $8 \times 10^7$ oligonucleotides/$cm^2$ in multispot arrays, with a dynamic range of greater than five orders of magnitude. This result was obtained without making any attempt to optimize hybridization efficiency, and represents a two to four order of magnitude improvement in sensitivity as compared to values provided in the literature for scanning SPR instruments without Au-colloid enhancement. The unoptimized sensitivity of microarray scanning SPR with Au colloid enhancement is at least comparable to that of conventional fluorophore-based methods for the detection of target DNA sequences in microarrays. However, use of the instruments, methods and reagents of the present invention will provide sensitivities that surpass fluorophore-based systems. Optimizing the improvements in Au colloid selection (e.g., size, shape, composition, etc.) and hybridization protocols (e.g., probe selection, annealing conditions, etc.) will be a routine task for those skilled in the art.

There have been significant improvements in the geometries for and approaches to creation of surface plasmons. Embodiments of the present invention directed to the implementation of some of these improvements are described below.

Simple SPR interferometers have been described in the literature. In the work of Kabashin and Nikitin, for example, a beam is split prior to Kretchsmann-geometry surface plasmon excitation and then recombined with the reflected light. Kabashin and Nikitin, Opt. Comm. 150: 5–8 (1998). The resulting interference pattern was imaged using a CCD. At the resonant angle of 43.7°, the minimum change in refractive index that could be detected was $\Delta n = 4 \times 10^8$, two orders of magnitude lower than can be detected by measurement of shifts in angle. In one embodiment of the present invention, the measurements can be performed using 12-nm diameter colloidal Au amplification, so that coverages of Au too low to be detected by shifts in angle (but clearly present based on AFM data) can be detected interferometrically. No detectable scattering is expected with such a low coverage of small nanoparticles.

In another embodiment of the present invention, the sensitivity of colloidal Au-amplified SPR may be improved by use of a "poor man's photonic crystal." Photonic crystals are materials that are completely opaque at certain wavelengths and completely transmissive at others. It has been shown that surface plasmons enhance optical transmission through subwavelength hole arrays in thin Ag films. Two anomalous effects have been observed: First, there are well-defined transmission minima and maxima, as would be expected for a photonic band-gap material. Second, the transmission through the holes is a thousand times greater than that predicted by standard aperture theory. This indicates that light flux at the holes is enhanced via coupling to surface plasmons. The present invention may take advantage of the enhanced coupling between the hole and a metal nanoparticle inside the hole. To do so, thin Ag films on glass with arrays of holes (of 100 nm in diameter) may be prepared similar to those described in the literature. The Ag surface may then be coated with an organothiol SAM to allow the glass beneath the hole to be selectively derivatized with capture antibody. A sandwich immunoassay may then be performed, with the secondary antibody tagged with a colloidal Au particle. Introduction of a colloidal Au particle then leads to a large change in the optical properties of the array of holes (e.g., reflectivity, transmittance). Even greater changes may be seen upon electroless growth of the particle to nearly fill the hole. Note that, since the film has been coated with an organoethiol SAM, metal will grow only on the particle.

In another embodiment of the present invention it is possible to simultaneously measure colloidal Au-SPR scattering over $2\pi$ and reflectivity as a function of angle. A CCD is mounted on a rotation stage, and can move with the hemispherical prism, allowing the scattered light to be measured at all angles. As a result, there will be an entire scattering image for each reflectivity data point. Three attributes of the data are important. First, because the photodiode collects both scattered and reflected light, measurement of the scattered intensity reaching the CCD at a given angle of incidence allows the scattered and reflected light to be distinguished. This is an essential prerequisite to understanding SPR reflectivity at surfaces with immobilized large particles, which exhibit both scattering and reflectivity components. Second, the scattering images themselves are used to determine the size (or sizes) of colloidal Au nanoparticles bound to the surface as well as to quantitate the number of particles bound. Third, there is an angular dependence and spatial distribution to the scattering. Both particle size and laser excitation angle profoundly impact scattering intensity.

Wet-chemistry synthesis of Au films.

The need for specific thicknesses of evaporated Au presents a significant barrier to high-throughput SPR substrate generation. To address this problem, the present invention provides a rapid wet-chemical approach to obtain thin Au films. The approach uses a "seeding" mechanism. In preferred embodiments, a seeded film is prepared by the selective reduction of $Au^{3+}$ ions from aqueous solution onto self-assembled monolayers of pre-formed colloidal Au particles. A detailed protocol for the wet chemical "seeding" of thin Au films is provided in Example 4.

PDMS microwell Arrays.

In order to quickly address multiple chemistries upon the same surface, a method is needed to physically separate each unique chemical interaction, enabling individual interrogation of each. One embodiment of the invention is directed to the fabrication and implementation of a polymeric, uniformly distributed, microwell array. The array of wells is biocompatible, extremely flexible, has very low chemical reactivity, can be attached to any substrate without use of adhesives, and is fabricated from inexpensive, readily available materials. These characteristics make the array an extremely flexible tool in implementing and analyzing arrayed chemistries, making it possible to carry out the simultaneous analysis of multiple surface chemistries by surface plasmon resonance (SPR). Such microwell array is also useful for analysis by ultraviolet-visible spectroscopy (UV-vis), surface enhanced Raman scattering, (SERS), and other surface-sensitive analytical techniques.

Recent years have seen a marked increase in the use of arrays as a tool in chemistry. The rapidly increasing use of combinatorial chemistry and its application in high throughput screening account for the majority of array usage in chemistry. Combinatorial chemistry is utilized in chemical areas as diverse as drug and inorganic compound discovery and novel material synthesis. Arrays have also been increasingly used as sensors to perform analysis of distinct compounds in a chemical mixture, with each individual sensor used to detect a unique compound. Alternatively, the individual sensors combine with the others in the sensor array to form a library of the ingredients in the addressed sample. Capillary electrophoresis columns arrayed on microchips is an example of an array adapted to an analytical technique.

Polydimethylsiloxane (PDMS) is a commercially available, inexpensive polymer possessing desirable properties for microwell arrays. The biocompatibility of PDMS makes it ideal for medical uses such as implants, artificial joints, contact lenses, and vascular and skin grafts. Industrial applications include electronics coatings and insulation, anti-foaming agents, media in carbon paste electrodes, micromachining, and microfabrication by microcontact printing (pCP) and micromolding in capillaries (MIMIC).

Figure 17A:
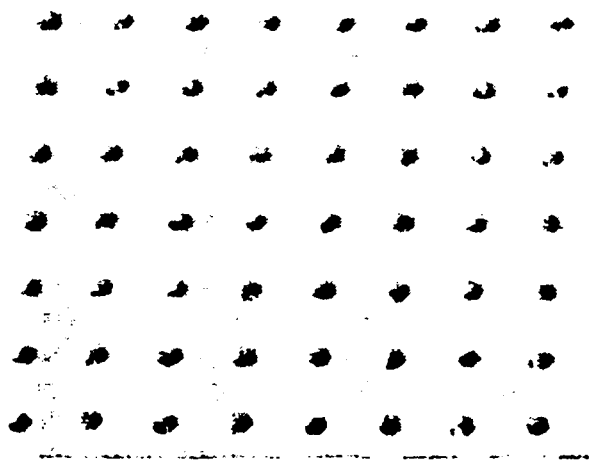
FIGS. 17A–17C depict components of the fabrication process of PDMS microwell arrays from top to bottom: (A) the one-inch square electronic breadboard "master", (B) the PDMS post "master", and (C) the PDMS well array replica of the electronic breadboard. The components were placed against a dark background to enhance the features formed from the colorless PDMS.
Figure 17B:
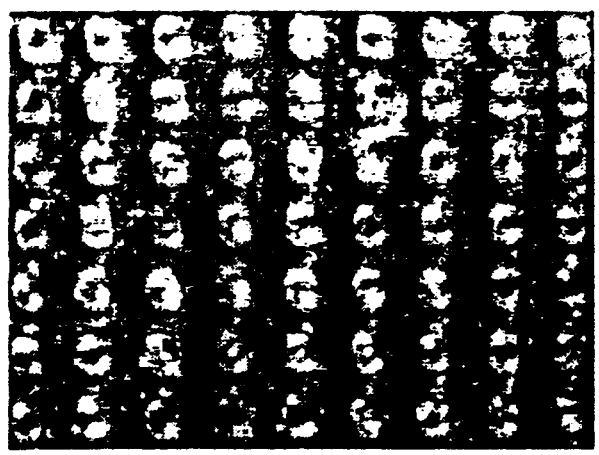
Figure 17C:
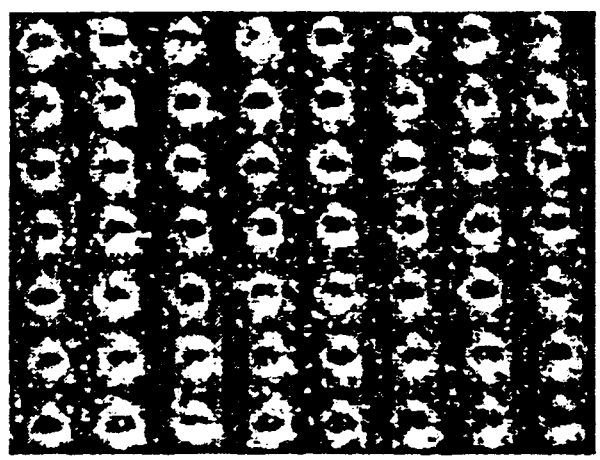
Figure 18A:
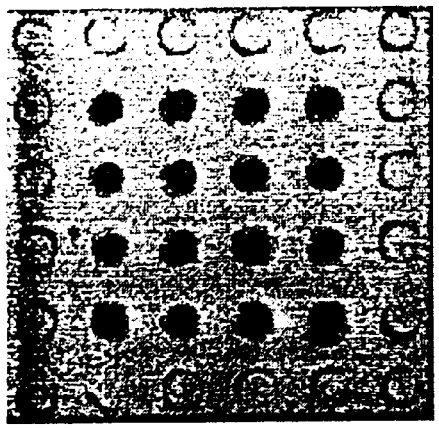
FIGS. 18A–18D depict time lapse photos of bromocresol blue in selected wells of the PDMS array: (A) Time=0, (B) Time=30 minutes, (C) Time=60 minutes, and (D) Time=24 hours.
Figure 18B:
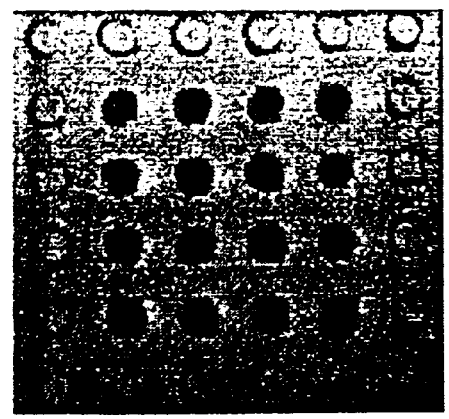
Figure 18C:
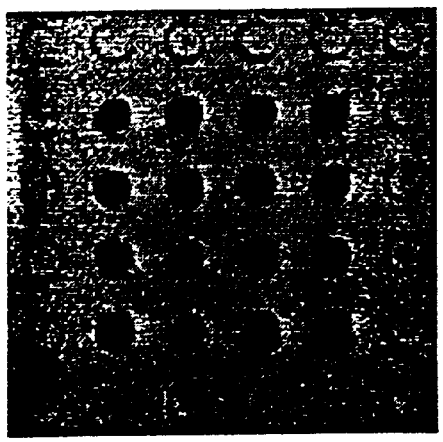
Figure 18D:
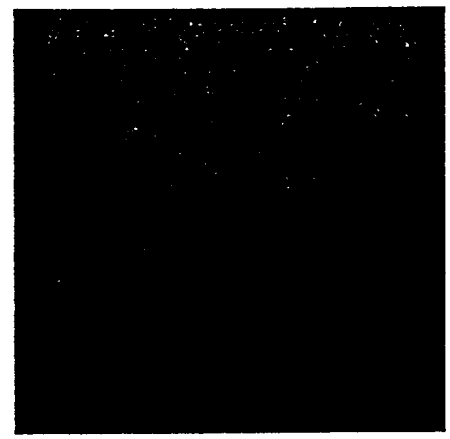

Fabrication of the PDMS microwell array of the present invention begins with the cutting of a section of electronic breadboard with a square pattern of 0.046-inch diameter holes spaced 0.092 inches on center. The PDMS prepolymer is then poured over the breadboard mold, and the prepolymer allowed to cure in a plastic petri dish. The PDMS-breadboard composite is then removed from the petri dish, and the components separated by hand. One of the potential problems with reproducing an array of this scale is that some of the posts become separated from the rest of the array. To prevent this, a light coating of release agent (e.g., Dow Corning 230 fluid) may be used on the breadboard mold. In addition, a thin layer of polymer may cure on the backside of the mold is easily shaved off with a razor blade. The PDMS "post array" cast is then used as a mold. Again, the mold is laid down in a petri dish (posts down) and PDMS is poured over it. Weight is placed on the mold to ensure proper contact of the post-tops with the petri dish surface. Again the prepolymer is cured. The PDMS "sandwich" is removed from the petri dish and separated. The new microwell array is then sonicated in soapy water followed by methanol for ten minutes each. FIG. 17 shows the results of each molding step.

Adhesion tests were conducted on glass, doped silicon, polycarbonate, and evaporated gold on glass. The well arrays were attached to the clean substrates by pressing them to the surface by hand and allowing electrostatic adhesion to take place. Designated wells were then filled with a 0.01 M aqueous solution of bromocresol blue with a pipette. Adhesion stability was recorded at 10, 20, 60, and 720 minute intervals. Even after 720 minutes of being attached to a given surface, no evidence of bromocresol blue leakage was observed on any of the substrates (FIG. 18).

The well array masters show a remarkable integrity, as several of the post masters have been used many times to replicate well arrays with seemingly no increase in structural defects. Post masters have been replicated from several different sizes and patterns, with equal success and minimization of defects. The hole sizes may range from 0.001 inches to 0.5 inches in diameter, preferably from 0.025 inches to 0.1 inches, with a density of holes up to 400 per square inch. Well arrays can be layered on top of one another and used to form post masters with longer posts from which arrays with deeper wells can subsequently be produced. Pigments may also be introduced into the elastomer, before curing, to produce colored well arrays. The use of colored arrays cuts down on stray and reflected light and therefore may be more useful in analyses where the light source is irradiated through the individual wells.

The PDMS well substrates of the present invention serve as an easily fabricated and implemented method of physically separating individual chemistries on a substrate. Each of these wells can be individually addressed and the surface chemical interactions analyzed without cross-contamination. Accordingly, these arrays can be readily adapted to virtually any surface analytical technique.

Reduction of background signal.

The main source of noise in SPR measurements is background signal, i.e. non-specific binding of colloidal Au. One approach to further improve the quality of the colloidal reagents includes coating Au nanoparticles with SAMs formed from mixtures of $HS(CH_2)_{15}CO_2H$ (10%) and $HS(CH_2)_{10}CH_2OH$ (90%), the same composition of thiols used to coat substrates. The carboxylates on the particles will stick out by a number of carbons and therefore can easily be activated by EDC, but the large preponderance of alcohol groups on the surface will preclude non-specific binding. Also, by appropriate dilution of carboxylate, it is possible to control the number of available biomolecule attachment sites. In addition, to circumvent the possibility that the quality of biomolecule:colloidal Au conjugates change over time, the biomolecule:particle probes may be lyophilized.

Other means to reduce nonspecific binding, particularly in DNA hybridization experiments, include: controlling the temperature, adding noncomplementary sequences, adjusting salt concentration, and reducing the solution concentration of DNA:Au conjugates during hybridization to surface oligos. To further decrease nonspecificity, longer linkers between DNA and the surface, both on colloidal Au particles and on the Au films may be used. Additionally, polyethylene glycol moieties can be covalently attached to carboxyl-terminated SAMs.

Increasing sensitivity by secondary amplification.

Increasing the magnitude of an Au nanoparticle-mediated change in reflectivity may be accomplished by directly amplifying the signal. This may be done by increasing the size of a colloidal Au nanoparticle that is brought in proximity to the SPR film via a binding reaction. Several different approaches to growth of immobilized colloidal Au nanoparticles, using both $Au^{3+}$ and $Ag^+$ (and appropriate reducing agents) have been demonstrated.

An alternative approach to direct amplification is to use a particle binding cascade, in which binding of a single particle triggers subsequent particle binding via specific nucleic acid (e.g., DNA) interactions. In one example, a colloidal Au "detection particle" (DP) is coated both with a monoclonal antibody that recognizes an antigen of interest and with a 30-base single-stranded DNA oligonucleotide (A). A first amplification particle (AP-1) comprising gold colloid coated with two single-stranded oligonucleotides (A' and B') is also prepared (e.g., by adding a mixture of biotinlyated oligos to streptavidin:Au), where A' is totally complementary to the oligonucleotide on the detection particle, while B' is totally non-complementary. Binding of the antigen to a capture antibody leads to binding of DP. Subsequent introduction of AP-1 into the solution will result in binding of multiple AP-1 particles to the DP. A second amplification particle (AP-2), coated with a single-stranded oligonucleotide (B) complementary to B', may then be introduced which will result in binding of multiple AP-2 particles to the AP-1 particles. Indeed, this cascade scheme may be expanded to include additional amplification particles.

It is important to note that the non-linear response of reflectivity and scattering vs. particle size means that the amplification is non-linear as well: three particles bound in close proximity so as to behave optically as a single large particle will yield changes far greater than those observed by binding of three isolated small particles. Moreover, while it is possible to induce an entire network of particles to bind to a single bound particle, such a network must necessarily have existed prior to binding to DP, as the DP cannot by itself induce networking. Since it is essential that there be no non-specific binding of DP, AP-1, or AP-2, an approach in which the cascade of nanoparticles is sequentially constructed is preferred to the task of eliminating non-specific binding of an aggregate.

An alternate cascade scheme may be used that does not require sequential addition of the amplification particles. This may be accomplished by designing the oligonucleotides attached to the amplification particles so that they are not complementary to each other, but are complementary to another single stranded segment of nucleic acid (e.g., DNA). This complementary oligonucleotide can be introduced into solution to activate the cascade that results in the binding of the amplification particles. For example, AP-1 may be coated with single stranded oligonucleotides B and C that are not complementary to each other or to A (which is coated on the DP). As described above, binding of the antigen to a capture antibody will result in binding of DP. However, AP-1 present in the solution will not bind to DP until single stranded oligonucleotide A'B' (complementary to oligos A and B) is introduced. Accordingly, AP-2 (which may also be present in the solution), coated with single-stranded oligonucleotide D, will not bind to AP-1 until oligonucleotide C'D' (complementary to oligos C and D) is introduced. As above, this cascade scheme may be expanded to include additional amplification particles. The advantage of this alternative scheme is that the amplification particles need not be added sequentially, but may be present in the solution from the start.

High-throughput screening of combinatorial libraries.

In one embodiment of the invention, particle-enhanced SPR is used in high throughput assays for libraries of small molecules. The combinatorial chemistry paradigm of drug discovery has created a situation where the design of functional assays is now rate-limiting, and few, if any, generally applicable solutions have been offered. The simplicity of SPR and its ability to be used in imaging mode make it an excellent choice.

High throughput applications require higher site density for SPR measurements. PDMS microwell arrays, with a "beaker" density of >100 per sq. inch, provide such higher density of sites. While repetitive pipetting of such small volumes may be inconvenient (or impossible) to perform manually, it may be accomplished by use of an arrayer robot. The approach involves using the robot's eight dispensing pins to deposit small spots of $HS(CH_2)_{11}CO_2H$. This molecule forms SAMs at those discrete locations on the substrate (i.e., where the dispensing pins came into close proximity). The remainder of the substrate is then filled in with $HS(CH_2)_{15}CH_3$, creating a hydrophobic environment around each (hydrophilic) spot. When the arrayer robot then dispenses an aqueous solution, it forms droplets over the hydrophilic patches, which provide the boundaries necessary to work at high site densities. An alternative solution is to use the robot's dispensing pins to mold a shape similar to them (but a bit larger) that can be filled with solvent.

EXAMPLE 1

Preparation of Evaporated Au Films and Au Colloid

The following materials and methods were used to obtain the data presented in FIGS. 1–5.

Au colloid of <12 nm diameter was prepared by citrate reduction of $HAuCl_4 \cdot 3H_2O$ as described in Grabar et al., J. Anal. Chem. 67: 735–743 (1995) and Grabar et al., J. Am. Chem. Soc. 118:1148–1153 (1996), each of which are incorporated by reference herein in their entirety.

Au colloid of >12 nm diameter was prepared by a modified "seed colloid" technique. 12 nm colloid (major axis 12 nm±2 nm and minor axis 11 nm±1 nm from 758 particles sized) in an amount of 1 mL was used as the starting material, with 100 mL, 0.01% HAuCl4 and 500 mL of 38.8 mM citrate solution. The resulting sample as analyzed by transmission electron microscopy (TEM) showed a major axis of 45 nm±5 nm and a minor axis of 37 nm±4 nm from 274 particles sampled. A second batch of large colloid produced using 100 mL of 0.02% $HAuCl_4$ and 1.0 mL of 38.8 mM citrate solution showed a major axis of 59 nm±14 nm and a minor axis of 52 nm±11 nm from 424 particles. Similar protocols produced batches of particles of the following dimensions: 30 nm±3 nm (major axis)×25 nm±2 nm (minor axis) from 373 particles sized and 35 nm±3 nm (major axis)×30 nm±3 nm (minor axis) from 112 particles sited. These preparations used 100 mL of 0.01% $HAuCl_4$ and 500 mL of 38.8 mM citrate solution with 3 mL and 2 mL of 12 nm diameter colloidal "seed" added, respectively. Average particle diameter and standard deviations were determined by particle size analysis of TEM Images using NIH Image: v.1.62 software.

Thin (47–50 nm) Au films were prepared by thermal evaporation of Au shot (99.99%, Johnson Mathey) from a resistively heated molybdenum boat (Kurt J. Lesker) in a diffusion-pumped Edwards Auto 306 thin-film fabrication system. Evaporation substrates were 1 inch×1 inch×0.02 inch, pieces of polished SF11 glass (n=1.78, Schott Glass Technologies) that had been exposed to a 10% (v/v) (3mercaptopropyl)-trimethoxysilane/$CH_3OH$ solution for 30 minutes in order to increase the adhesion of Au to the glass. Au was deposited at a pressure of $1 \times 10^{-6}$ mbar at 0.5 nm/s with constant sample rotation to ensure uniform deposition. Following evaporation, the films were annealed in a home-built oven at 300° C. for 5–10 minutes under a constant flow of argon to decrease the surface roughness of the evaporated layer.

Annealed Au films were modified with alkanethiols (2-mercaptoethylamine (MEA) or 3-mercaptopropionic acid (MPA)) from 10 mM ethanolic solutions for a period of 30 min. Longer immersion times did not noticeably improve the efficiency or density of subsequent derivitization steps. Immobilization of colloidal Au onto amine modified (MEA coated) surfaces was performed from undiluted aqueous solutions at room temperature. Amine-modified surfaces induce the strong adsorption of colloidal Au particles by virtue of the availability of an electron lone pair on the amine nitrogen, as well as ionic interactions with the negatively charged particles.

SPR data was obtained using a scanning SPR instrument. Excitation of the surface plasmon is accomplished using the Kretschmann geometry where a 1 inch diameter hemispherical prism (SF11 glass, Esco Products) is index matched (Cargille immersion oil, n=1.78) to a SF11 substrate onto which Au had been previously evaporated as described above. This assembly is then affixed to a home-built flow cell (volume ~100 mL) with the Au film exposed to solution. The SPR excitation source is a cylindrical 5 mW, 500:1 polarization extinction HeNe laser (632.8 nm, Melles Griot) which is further polarized by a 500:1 visible-optimized linear polarizer (Newport 10LP-VIS). An optical chopper (Stanford Research Systems) is used to modulate the optical signal at a frequency of 2 kHz, which was then correlated with detection via a lock-in amplifier (Stanford Research Systems, SR530). The beam is focused by a 100-mm focal length (fl) plano-convex (PCX) tens and recollimated by a 25-mm fl PCX lens, thereby reducing the beam size to 0.4 mm±0.1 mm in diameter. A hemispherical lens is then used to focus the beam such that it is recollimated by the hemispherical prism-sample assembly. The reflected beam is then passed through an iris and focused onto a silicon photodiode detector (Thor Labs), the signal from which is then measured with the lock-in amplifier that is in-phase with the excitation source. Angular positioning of the sample is accomplished with a home-built θ-2θ stage consisting of two high-resolution (0.001°) servo-drive rotation stages (Newport, RTM80CC and RTM160CC annular rotary stages) that are mounted together such that their axes of rotation are collinear. The prism/sample/flow cell assembly is then mounted on the θ-2θ stage such that the center of the Au/glass sample is at the axis of rotation. Stage rotation and data collection are controlled through a computer interface that was developed using the LabVIEW programming language (version 4.01, National Instruments). A typical SPR scan was run at either 0.1 or 0.01° resolution, a stage rotation rate of 0.5° $s^{-1}$, and a lock-in time constant of 0.3 s.

Particle densities were determined using Tapping mode atomic force microscopy (TM-AFM) images acquired using a Digital Instruments Nanoscope IIIA operated in tapping mode with an acquisition frequency of 1.5 Hz and line density of 512. Standard 200 nm etched silicon probes were used for the purposes of coverage determination. At least four images were obtained from two distinct regions of each sample. Two 5 $\mu$m×5 $\mu$m images were taken ~0.5 mm apart to confirm that the surface coverage was homogeneous. At each position, 1 $\mu$m×1 $\mu$m scans were captured in order to obtain higher resolution images. Particle counting was done manually from captured images. Reported numbers are average coverage values obtained from 2 to 3 images.

In all experiments, care was taken to ensure that the identical region of a particular sample was interrogated with both SPR and TM-AFM. Accordingly, a box was scratched around the area illuminated during the SPR experiment. The surface coverage within that area was then measured via AFM, thereby alleviating any errors due to uneven surface derivatization over large length scales. It is important to note that the solution agitation is an important step in obtaining particle-diameter-independent coverage values. At short exposure times (<1 hour) and identical solution particle concentrations, approximately equal particle surface concentrations may be obtained independent of colloid diameter. This removes the diffusion dependence of surface attachment and leaves the sticking probability (which is only slightly influenced by particle diameter) as the determining factor in the resultant particle number density.

EXAMPLE 2

Sandwich Immunoassays

The following materials and methods were used to obtain the data presented in FIGS. 6–10.

Au film and Au colloid were prepared as described above. Human IgG (h-IgG), γ-chain-specific monoclonal goat anti-human IgG antibody [a-h-IgG (γ)] and $F_c$ specific monoclonal goat anti-Human immunoglobulin G antibody [a-h-IgG($F_c$)] were obtained from Sigma Immunochemicals.

Protein-Au conjugates were synthesized by the addition of a-h-IgG ($F_c$) to 5 mL of pH-adjusted colloid followed by incubation on ice with periodic gentle mixing for 1 hour. The conjugate was then divided into 1 mL fractions in 1.5 mL, micro-centrifuge tubes and centrifuged at 12,500 g for 45 minutes (Heraeus picoBiofuge). The clear to pink supernatant was removed and the soft pellet resuspended to an optical density of ~3 into $H_2O$ or 40 mM phosphate buffer (pH 7.0). Conjugates can be stored between 2 and 8° C. for several days without loss of activity.

A flocculation profile was constructed for a-h-IgG ($F_c$)-Au colloid conjugates to determine the amount of protein that was necessary to coat the exterior of the Au particle, and hence inhibit colloid aggregation. Solutions were prepared from 0.75 mg/mL stock solution aliquots (0–72 μg) of a-h-IgG ($F_c$) and were added in 6 μg increments to cuvettes containing 1.0 mL of 10 nm diameter colloid solution adjusted to pH 8.0 (EM Science color-pHast indicator strips, pH 2–9) using 0.1 M NaOH. The samples were volume-corrected to 1.150 mL with deionized $H_2O$ and 150 μL of 1.0 M NaCl was added to each. The solutions were agitated and optical spectra recorded after 10 min. For a 10 nm colloid, 31.5 μg of a-h-IgG ($F_c$)/mL of colloid was determined to inhibit aggregation.

To immobilize a-h-IgG (γ) (and other proteins) on the Au film, the Au surface was modified with MPA as described above in order to introduce carboxylate groups onto the Au surface. Formation of an active ester at the Au surface was then achieved by reacting 100 μL of a 100 mM, pH 5.5, (1-ethyl-3-(3-(dimethylamino)propyl)carbo-diimide hydrochloride (EDC) solution with the carboxylated Au surface for 15 minutes. A 50 μL aliquot of Sulfo-N-hydroxysuccinimide (S-NHS) (40 mM, pH 7) is then injected into the flow cell to stabilize the reactive surface through displacement of the imide moiety. After 15 minutes of incubation with S-NHS, the cell is rinsed with 10 mL of buffer (85 mM phosphate, pH 7) and a 1.0 mg/mL solution of the protein to be immobilized is injected. The surface is incubated with the protein solution for 30 min and is then washed with another 10 mL of phosphate buffer. Unreacted sites on the surface are then blocked by reaction with a 10 mg/mL solution of bovine serum albumin. After another buffer wash, immunochemical reactions may be performed; typical incubation times for antigen and conjugate solutions range from 5 to 30 minutes. All SPR profiles were acquired as described in Example 1 in buffer to eliminate slight index of refraction differences that may exist between protein solutions.

EXAMPLE 3

DNA Detection

The following materials and methods were used to obtain the data presented in FIG. 13.

Trisodium citrate dihydrate, poly(ethylene glycol) bis(3-aminopropyl) terminated (PEG), 16-mercaptohexadecanoic acid (90%) (MHA), 3-mercapto-propionic acid (MPA), ethylenediaminetetraacetic acid (EDTA), and NaOH were obtained from Aldrich. $HAuCl_4.3H_2O$ was obtained from Acros. $NaH_2PO_4$, $Na_2HPO_4$, sodium dodecyl sulfate (SDS, 95%), NaCl, KCl, concentrated $HCl$, $HNO_3$, $H_2SO_4$, and 30% $H_2O_2$ were purchased from J. T. Baker Inc. 3-Mercaptopropylmethyldimethoxysilane (MPMDMS) and 3-aminopropyl-trimethoxysilane (APTMS) were purchased from United Chemical Technologies. $MgCl_2$, spectrophotometric grade $CH_3COH$, and $CH_3OCH_3$ were obtained from EM Science. $CH_3CH_2OH$ was purchased from Pharmco. 1-ethyl-3-(3-dimethylaminopropyl)carbodiimide (EDC), N-hydroxysulfosuccinimide (NHS), and streptavidin were from Pierce. The restriction enzyme Hinf I was purchased from Biolabs. HPLC purified oligonucleotides were purchased from Integrated DNA Technology or from the Pennsylvania State University Nucleic Acid Facility (Chart I). All reagents were used as received without further purification. $H_2O$ used was distilled and subsequently purified using a Barnstead Nanopure system. Hybridization buffer was prepared with 0.3 M NaCl in a 10-mM phosphate (pH 7.0) buffer. 10 μM non-complementary 12-mer oligonucleotides were added as the blocking reagent. 25-mM Tris-HCl (pH 7.8), 100-mM KCl, 10-mM $MgCl_2$ were mixed and used as the enzyme buffer. Au (99.99%) shots and Cr wires used for evaporation were obtained from Johnson-Matthey Corp. SF11 glass slides (Schott Glass Technologies, n=1.78) were used in the SPR scanning experiments, and Fisher Precleaned microscope slides (BK7, n=1.515) were used in the imaging experiments.

DNA:Au conjugate preparation. 12-nm diameter colloidal Au was prepared by citrate reduction of $HAuCl_4.3H_2O$ as described in Example 1. Average particle diameters were determined by transmission electron microscopy (TEM), which showed a standard deviation less than 10%. Optical spectra of colloidal Au solutions were recorded using a HP 8453 spectrophotometer.

Thiol-labeled DNA:Au conjugates were prepared according to protocols described in Mirkin et al., Nature 382: 607–609 (1996), Elghanian et al., Science 277:1078–1081 (1997), Storhoff et al., J. Am. Chem. Soc. 120:1959–1964 (1998), Storhoff & Mirkin, .Chem. Rev. 99:1849–1862 (1999), and Mucic et al., J. Am. Chem. Soc. 120: 12674–12675 (1998), each of which is incorporated herein by reference it its entirety. 36 μl of 12-mer (100 μM) oligonucleotide probe SEQ ID NO:3 was added to 1-ml Au colloid solution. After standing for 16 hrs, the solution was aged in a 0.1 M NaCl solution (pH 7, 10-mM phosphate buffer) for 2 days. The DNA:Au conjugate was then washed by centrifugation (45 min, 12,500×g) to remove excess reagents. The supernatant was disposed, followed by washing the red pellet with 0.1 M NaCl. After a second centrifugation, the pellet was brought to the original concentration in a 0.3 M NaCl/phosphate hybridization solution. The conjugates were used freshly as prepared, and an optical spectrum was always taken to ensure consistent solution concentration.

Biotinylated DNA:Au conjugates can be prepared from streptavidin:Au conjugate. A solution of Au particles diluted 1:1 in $H_2O$ and adjusted to pH 8.5 with 0.1 M NaOH was added to 40 RI of 1 mg/ml streptavidin stock solution. After incubating on ice for 1 hr, the solution was centrifuged (12,500× g, 45 min) to separate unbound protein. 200 μL of a biotinylated oligo probe (10 μM ) was then incubated with the conjugate for 30 min followed by a second centrifugation with removal of the supernatant and resuspension into hybridization buffer. Again, an optical spectrum was taken to ensure consistent solution concentration as performed with the thiol-labeled DNA conjugates.

Successful incorporation of oligonucleotide probes onto the surface of Au colloid was verified using a method described in Mirkin et al., Nature 382: 607–609 (1996), Elghanian et al., Science 277:1078–1081 (1997), Storhoff et al., J. Am. Chem. Soc. .120:1959–1964 (1998), and Storhoff & Mirkin, Chem. Rev. 99:1849–1862 (1999). In short, SEQ ID NO:3:Au conjugate solutions were mixed with a linking oligonucleotide that can hybridize to two different copies of SEQ ID NO:3, and then flocculation induced by the linking oligonucleotide was monitored. While the optical spectrum of the mixture exhibited the characteristic absorbance of Au colloid at 524 nm, the addition of a linking oligonucleotide led to a redshift of $\lambda_{max}$, accompanied by a significant decrease in intensity. This is due to the formation of nanoparticle aggregates. By gradually increasing the solution temperature above the melting point of the DNA duplex, dehybridization occurred and resulted in the dissociation of the colloidal Au network. Consequently, an increase in the optical intensity at 260 nm, a signature absorbance of free oligonucleotides in solution, was observed. DNA:Au conjugates which did not show reversible flocculation in this test were discarded.

Au surfaces were prepared as detailed in Example 1. A self-assembled monolayer was affixed to the Au surface through an overnight immersion in a 10-mM MHA/$C_2H_5OH$ solution. An amine-labeled 12-mer oligonucleotide (SEQ ID NO:1), with a sequence complementary to half of the target SEQ ID NO:2, was coupled to the carboxylate groups on the surface via EDC/NHS cross-linking. Amine-labeled PEG (1%) was then introduced to block unreacted sites, followed by rinsing and the incubation of the target analyte, a 24-mer DNA (SEQ ID NO:2), in hybridization buffer for 2 hrs. In the unamplified experiment, an untagged DNA probe (SEQ ID NO:3), with sequence complementary to the other half of SEQ ID NO:2, was added and incubated with the surface. In the amplified event, however, the SPR surface was exposed to the Au particle-tagged SEQ ID NO:3 probes. In both cases, hybridization was carried out for 1 hr, followed by extensive rinsing with a 0.2% SDS/0.1 M NaCl buffer.

Scanning SPR data was acquired using the instrument as described in Example 1. A miniature peristaltic pump (Intech Laboratories, Inc.) was used to deliver analyte solutions to the sample cell at 0.1 ml/min. A 5-min $H_2O$ rinse at 1 ml/min was always carried out before collecting SPR measurements. All experiments were completed at room temperature except for DNA melting, in which the temperature of the sample cell was increased by flowing warm dehybridization buffer (80° C. as measured at the water bath) for 20 min. A much higher temperature, 27° C. above the melting point of the surface-confined DNA duplex, was applied here due to thermal gradients in the liquid delivery apparatus. The actual temperature at the surface is estimated to be between 60 and 70° C. The sample cell was cooled down to room temperature before the SPR measurement. Kinetic studies were carried out by monitoring SPR reflectivity changes as a function of incubation time at a fixed angle (53.2°).

Imaging SPR was carried out using the instrument described above. Data were plotted as spatial intensity maps of the SPR substrate surface, where an increase in intensity indicates an increase in SPR response. A commercial software package, NIH Image, was used for image analysis. From the spatial intensity map the integrated intensity from each sample cell was calculated, a baseline intensity was subtracted, and each signal was normalized for the area of the sample cell.

UV-Vis Absorbance Spectroscopy: UV-vis spectra were collected using a HP 8453 diode array spectrophotometer equipped with a HP 89090A Peltier temperature controller. By changing the solution temperature from 25–65° C. at 1° C./step, a DNA melting assay was tested by monitoring the optical intensity changes at 260 nm. Hybridization buffer was used as the blank.

EXAMPLE 4

Wet Chemical Synthesis of Thin Au Films

Glass coverslips (n=1.515, Fisher) were washed by immersion in a 'piranha' bath (30% $H_2O_2$ mixed in a 1:4 ratio with concentrated $H_2SO_4$. Caution should be used in handling this solution as it is extremely oxidizing). The clean glass slides were then functionalized with a self assembled mono-layer of (3-mercaptopropyl)methyl-dimethoxysilane (MPMDMS, United Chemical Technologies) by exposure to a 1–10 mM ethanolic solution of the silane for 30 minutes. A functionalized slide was then placed in a 17 nM solution of 12 nm diameter colloidal Au until a surface coverage that yielded an absorbance of 0.1 AU at 520 nm was obtained. The colloidal Au-modified surface was then placed in 500 mL of aqueous 0.5 mM $NH_2OH.HCl$ (Aldrich), to which 100 mL of 0.06% $HAuCl_4$ (Acros) was added while agitating on an orbital shaker at 150 revs/minute. Agitation was continued for 20 minutes to produce a smooth, reflective Au surface on the monolayer.

EXAMPLE 5

Synthesis of PDMS Microwell Array

Film thicknesses were determined by measuring the step height at a scribed spot on the surface via tapping-mode atomic force microscopy (TM-AFM) as described in Example 1 using standard 200 µm etched silicon probes, an acquisition frequency of 1.5 Hz, and line density of 512.

PDMS (Dow Corning Sylgard 184 in a 10:1 ratio of elastomer to hardener) is mixed, degassed using a vacuum dessicator, and poured over a one inch square electronic breadboard master into a small petri dish. This composite is degassed using a vacuum dessicator and then cured overnight in a 50° C. oven. After cooling, the new PDMS "master" is peeled away from the electronic breadboard. This new "master" is used to form the final mold of PDMS. Additional PDMS is then poured in between the new master and the petri dish, degassed, and cured in an oven overnight. An aluminum block, attached to a glass microscope slide is placed on top as a weight to assure constant contact with the bottom of the petri dish. This PDMS sandwich is removed from the oven, cooled, and then peeled apart revealing the PDMS replica of the electronic breadboard.

What is claimed is:

1. A method for conducting a plurality of assays for a plurality of different analytes in a test solution that may contain said different analytes, comprising:

providing a surface plasmon resonance active surface;

associating a plurality-of different ligands to said different analytes to said surface;

contacting said surface with said test solution, wherein the presence or absence of a specific analyte results in a specific type of colloidal metal nanoparticle associating with a specific type of ligand at or near said surface, wherein different ligands associate with different types of colloidal metal nanoparticles; and detecting for said associations between said different ligands and said different types of colloidal metal nanoparticles by measuring the SPR profile, wherein the SPR profile is distinguishable between said different types of colloidal metal nanoparticles.

2. The method of claim 1 wherein said different types of colloidal metal nanoparticles are distinguished by their size.

3. The method of claim 1 wherein said different types of colloidal metal nanoparticles are distinguished by their composition.

4. The method of claim 1 wherein said surface plasmon resonance active surface is a thin metal film.

5. The method of claim 4 wherein said thin metal film is selected from the group consisting of Au, Ag, Al and Cu.

6. The method of claim 4 wherein said thin metal film is coated on a glass surface.

7. The method of claim 1 wherein said colloidal metal nanoparticles are comprised of a metal selected from the group consisting of Au, Ag, Al and Cu.

8. The method of claim 1 wherein said colloidal metal nanoparticles are substantially spherical.

9. The method of claim 8 wherein said colloidal metal nanoparticles are 1 nm to 150 nm in diameter.

10. The method of claim 1, wherein at least one of said different types of colloidal metal nanoparticles comprises an AuS/Au shell particle.

* * * * *